United States Patent
Rafii et al.

(10) Patent No.: US 11,913,021 B2
(45) Date of Patent: *Feb. 27, 2024

(54) METHODS AND COMPOSITIONS FOR PROMOTING SURVIVAL AND PROLIFERATION OF ENDOTHELIAL CELLS AND STIMULATING ANGIOGENESIS

(71) Applicants: Cornell Research Foundation, Inc., Ithaca, NY (US); Sloan-Kettering Institute for Cancer Research, New York, NY (US)

(72) Inventors: Shahin Rafii, New York, NY (US); Fan Zhang, Fort Lee, NJ (US); Marco Seandel, New York, NY (US)

(73) Assignees: Cornell Research Foundation, Inc., Ithaca, NY (US); Sloan-Kettering Institute for Cancer Research, New York, NY (US)

( * ) Notice: Subject to any disclaimer, the term of this patent is extended or adjusted under 35 U.S.C. 154(b) by 362 days.

This patent is subject to a terminal disclaimer.

(21) Appl. No.: 17/099,122

(22) Filed: Nov. 16, 2020

(65) Prior Publication Data

US 2021/0155899 A1 May 27, 2021

Related U.S. Application Data

(63) Continuation of application No. 15/906,408, filed on Feb. 27, 2018, now Pat. No. 10,865,379, which is a
(Continued)

(51) Int. Cl.
*C12N 5/0735* (2010.01)
*C07K 14/005* (2006.01)
(Continued)

(52) U.S. Cl.
CPC .......... *C12N 5/0606* (2013.01); *C07K 14/005* (2013.01); *C12N 5/069* (2013.01);
(Continued)

(58) Field of Classification Search
CPC .. C07K 14/005; C12N 5/069; C12N 15/1131; C12N 15/1136; C12N 5/0606;
(Continued)

(56) References Cited

U.S. PATENT DOCUMENTS 6,140,087 A 10/2000 Graham et al.
6,475,480 B1 11/2002 Mehtali et al.
(Continued)

FOREIGN PATENT DOCUMENTS

WO 02/36829 A2 5/2002

OTHER PUBLICATIONS

Ackah, E. et al., "Akt1/protein kinase Bα is critical for ischemic and VEGF-mediated angiogenesis," The Journal of Clinical Investigation, http://www.jci.org, vol. 115, No. 8, pp. 2119-2127 (Aug. 2005).
(Continued)

*Primary Examiner* — Sean C. Barron
(74) *Attorney, Agent, or Firm* — Scully, Scott, Murphy & Presser, P.C.

(57) ABSTRACT

The present invention relates to adenovirus E4ORF1 gene and to endothelial cells engineered to express the E4ORF1 gene. The present invention also relates to uses of the E4ORF1 gene, and cells expressing the E4ORF1 gene, and to compositions comprising the E4ORF1 gene, or comprising cells expressing the E4ORF1 gene.

20 Claims, 11 Drawing Sheets

Specification includes a Sequence Listing.

Related U.S. Application Data continuation of application No. 13/897,829, filed on May 20, 2013, now Pat. No. 9,944,897, which is a continuation of application No. 12/523,372, filed as application No. PCT/US2008/051499 on Jan. 18, 2008, now Pat. No. 8,465,732.

(60) Provisional application No. 60/881,667, filed on Jan. 22, 2007, provisional application No. 60/881,225, filed on Jan. 19, 2007.

(51) Int. Cl.
| | |
|---|---|
| C12N 5/071 | (2010.01) |
| C12N 15/113 | (2010.01) |
| C12N 5/0789 | (2010.01) |
| C12N 5/09 | (2010.01) |

(52) U.S. Cl.
CPC ......... *C12N 5/0647* (2013.01); *C12N 5/0693* (2013.01); *C12N 15/1131* (2013.01); *C12N 15/1136* (2013.01); *C12N 2310/14* (2013.01); *C12N 2501/998* (2013.01); *C12N 2710/10322* (2013.01); *C12N 2740/10043* (2013.01)

(58) Field of Classification Search
CPC ............... C12N 5/0647; C12N 5/0693; C12N 2310/14; C12N 2501/998; C12N 2710/10322; C12N 2740/10043
See application file for complete search history.

(56) References Cited

U.S. PATENT DOCUMENTS

| | | | |
|---|---|---|---|
| 6,485,958 B2 | 11/2002 | Blanche et al. | |
| 6,730,662 B1 | 5/2004 | Branton et al. | |
| 8,465,732 B2 * | 6/2013 | Rafii ...................... | C12N 5/069 |
| | | | 435/325 |
| 9,944,897 B2 | 4/2018 | Rafii et al. | |
| 2002/0165193 A1 | 11/2002 | Greene et al. | |
| 2010/0055678 A1 | 3/2010 | Risti | |

OTHER PUBLICATIONS

Avecilla, S.T. et al., "Chemolkine-mediated interaction of hematopoietic progenitors with the bone marrow vascular niche is required for thrombopoiesis," Nature Medicine, vol. 10, No. 1, pp. 64-71 (Jan. 2004).

Bridge, E. et al., "Interaction of Adenoviral E4 and E1 b Products in Late Gene Expression," Virology 174, 345-353 (1990).

Bridge, E. et al., "Redundant Control of Adenovirus Late Gene Expression by Early Region 4," Journal of Virology, pp. 631-638, vol. 63, No. 2 (Feb. 1989).

Brunet, A. et al., "Transcription-dependent and -independent control of neuronal survival by the PI3K-Akt signaling pathway," Curr Opin Neurobiol, 11(3):297-305 (2001).

Calabrese, C. et al., "A Perivascular Niche for Brain Tumor Stem Cells," Cancer Cell 11, 69-82, (Jan. 2007).

Chen, J. et al., "Akt1 regulates pathological angiogenesis, vascular maturation and permeability in vivo," Nature Medicine, vol. 11, No. 11, pp. 1188-1196 (Nov. 2005).

Chung, S.H. et al., "A New Crucial Protein Interaction Element That Targets the Adenovirus E4-ORF1 Oncoprotein to Membrane Vesicles," Journal of Virology, p. 4787-4797, vol. 81, No. 9 ( May 2007).

Craven, S.E. et al., "PDZ Proteins Organize Synaptic Signaling Pathways," Cell, vol. 93, 495-498 (May 15, 1998).

Crystal, R.G. et al., "Administration of an adenovirus containing the human CFTR cDNA to the respiratory tract of individuals with cystic fibrosis," Nature Genetics, vol. 8, pp. 42-51 (Sep. 1994).

Crystal, R.G., "Transfer of genes to humans: Early lessons and obstacles to success", Science, v270, 0404-410 (1995).

Deroanne, C.F. et al., "In vitro tubulogenesis of endothelial cells by relaxation of the coupling extracellular matrix-cytoskeleton", Cardiovascular Research, 49:647-658 (2001).

Deonarain, M.P., "Ligand-targeted receptor-mediated vectors for gene delivery", Expert Opinion on Therapeutic Patents, 8(1):53-69 (1998).

Dias, S. et al., "Inhibition of both paracrine and autocrine VEGFNEGFR-2 signaling pathways is essential to induce long-term remission of xenotransplanted human leukemias," PNAS, vol. 98, No. 19, 10857-10862 (Sep. 11, 2001).

Dobrosotskaya, I.Y. et al., "MAGI-1 Interacts with ?-Catenin and Is Associated with Cell-Cell Adhesion Structures," Biochemical and Biophysical Research Communications 270, 903-909 (2000).

Drexler, H.G. et al., "False leukemia-lymphoma cell lines: an update on over 500 cell lines," Leukemia, 17, 416-426 (2003).

Dull, T. et al., "A Third-Generation Lentivirus Vector with a Conditional Packaging System," Journal of Virology, vol. 72, No. 11, p. 8463-8471 (Nov. 1998).

Fabry, C.MS. et al., "A quasi-atomic model of human adenovirus type 5 capsid", The EMBO Journal, 24, pp. 1645-1654. (2005).

Fanning, A.S. et al., "PDZ domains: fundamental building blocks in the organization of protein complexes at the plasma membrane", The Journal of Clinical Investigation, vol. 103, No. 6, pp. 767-772 (Mar. 1999).

Frese, K.K. et al., "Selective PDZ protein-dependent stimulation of phosphatidylinositol 3-kinase by the adenovirus E4-ORF1 oncoprotein," Oncogene, 22, 710-721 (2003).

Gilbertson, R.J. et al., "Making a tumour's bed: glioblastoma stem cells and the vascular niche," Nature Reviews, Cancer, vol. 7, pp. 733-736 (Oct. 2007).

Glaunsinger, B.A. et al., "Interactions of the PDZ-protein MAGI-1 with adenovirus E4-0RF1 and high-risk papillomavirus E6 oncoproteins," Oncogene, 19, 5270-5280 (2000).

Hersh, J. et al., "Modulation of gene expression after replication-deficient, recombinant adenovirus-mediated gene transfer by the product of a second adenovirus vector," Gene Therapy, 2, 124-131 (1995).

Ingram, D.A. et al., "Identification of a novel hierarchy of endothelial progenitor cells using human peripheral and umbilical cord blood," Blood, 104: 2752-60 (2004).

Ingram, D. A. et al., "Unresolved questions, changing definitions, and novel paradigms for defining endothelial progenitor cells," Blood 106: 1525-1531 (2005).

Johnson-Saliba, M. et al., Gene Therapy: Optimizing DNA Delivery to the Nucleus, Current Drug Targets, v2, p. 371-399 (2001).

Kiel, M.J. et al., "SLAM Family Receptors Distinguish Hematopoietic Stem and Progenitor Cells and Reveal Endothelial Niches for Stem Cells," Cell, vol. 121, 1109-1121 (Jul. 1, 2005).

Koizumi, K. et al., "Incorporation adult organ-derived endothelial cells into tumor blood vessel," Biochemical and Biophysical Research Communications, 306, 219-224 (2003).

Lammert, E. et al., "Induction of Pancreatic Differentiation by Signal from Blood Vessels," Science, vol. 294, pp. 564-567 (Oct. 19, 2001).

Leppard, K., "E4 gene function in adenovirus, adenovirus vector and adeno-associated virus infections", Journal of General Virology, v78, p. 2131-2138 (1997).

Liu, Q. et al., "Aki/Protein Kinase B Activation by Adenovirus Vectors Contributes to NFKB-Dependent CXCL 10 Expression," Journal of Virology, pp. 14507-14515, vol. 79, No. 23 (Dec. 2005).

Meredith, Jr., J.E. et al., "The Extracellular Matrix as a Cell Survival Factor," Molecular Biology of the Cell, vol. 4, 953-961 (Sep. 1993).

Miller, N. et al., "Targeted vectors for gene therapy", FAS EB J., v9, 190-199 (1995).

Mukai, Y. et al., "Decreased vascular lesion formation in mice with inducible endolhelialspecific expression of protein kinase Aki," The Journal of Clinical Investigation, vol. 116, No. 2, pp. 334-343 (Feb. 2006).

Nikolova, G. et al., "The Vascular Basement Membrane: A Niche for Insulin Gene Expression and? Cell Proliferation," Developmental Cell, 10, 397-405 (Mar. 2006).

(56) References Cited

OTHER PUBLICATIONS

Ojeifo, J.O. et al., "Angiogenesis-directed Implantation of Genetically Modified Endothelial Cells in Mice", Cancer Research, v55, p. 2240-2244 (1995).
Ortega, S. et al., "Neuronal defects and delayed wound healing in mice lacking fibroblast growth factor 2," Proc. Nall. Acad. Sci. USA, vol. 95, pp. 5672-5677, Genetics (May 1998).
O'Shea, C. et al., "Adenoviral proteins mimic nutrient/growth signals to activate the mTOR pathway for viral replication", The EMBO Journal, vol. 24, pp. 1211-1221 (2005).
Parolari, A. et al., "Hypertonicity Induces Injury to Cultured Human Endothelium: Attenuation by Glutamine", Ann Thorac Surg, v64, p. 1770-1775 (1997).
Pfeifer, A. et al., "Gene Therapy: Promises and Problems", Annu. Rev. Genomics Hum. Genet., v2, p. 177-211 (2001).
Phung, T.L. et al., "Endothelial Aki Signaling Is Rate-Limiting for Rapamycin Inhibition of Mouse Mammary Tumor Progression," Cancer Res 2007; 67 (11), pp. 5070-5075 (Jun. 1, 2007).
Phung, T.L. et al., "Pathological angiogenesis is induced by sustained AKI signaling and inhibited by rapamycin," Cancer Cell, 10 (2): 159-170 (Aug. 2006).
Querido, E. et al., "Regulation of p53 Levels by the E 1 B 55-Kilodalton Protein and E40rf6 in Adenovirus-Infected Cells," Journal of Virology, vol. 71, No. 5, p. 3788-3798 (May 1997).
Rafii, S. et al., "Human Bone Marrow Microvascular Endothelial Cells Support Long-Term Proliferation and Differentiation of Myeloid and Megakaryocytic Progenitors," Blood, 86:3353-3363 (1995).
Rafii, S. et al., "Isolation and characterization of human bone marrow microvascular endothelial cells: hematopoietic progenitor cell adhesion," Blood, 84: 10-19 (1994).
Rafii, S. et al., "Infection of Endothelium With El-E4+, but Not EI-E4−, Adenovirus Gene Transfer Vectors Enhances Leukocyte Adhesion and Migration by Modulation of ICAM-1, VCAM-1, CD34, and Chemokine Expression", Circulation Research, v88, p. 903-910 (2001).
Rafii, S. et al., "Human ESC-derived Hemogenic Endothelial Cells Undergo Distinct Waves of Endothelial to Hematopoietic Transition" Blood, vol. 121 (5): 770-780, Published online Nov. 20, 2012 America Society of Hematology, Washington, DC (Jan. 31, 2013).
Rajala, M.S. et al., "Corneal Cell Survival in Adenovirus Type 19 Infection Requires Phosphoinositide 3-Kinase/Akt Activation," Journal of Virology, 79(19):12332-12341 (2005).
Ramalingam, R. et al., "Downregulation of CXCR4 Gene Expression in Primary Human Endothelial Cells Following Infection with E1-E4+ Adenovirus Gene Transfer Vectors," Molecular Therapy, vol. 2, No. 4, pp. 381-386 (Oct. 2000).
Ramalingam, R. et al., "E1-E4+ Adenoviral Gene Transfer Vectors as a "Pro-Life" Signal to Promote Survival of Primary Human Endothelial Cells," Blood, vol. 93, No. 9, pp. 2936-2944 (May 1, 1999).
Ramalingam, R. et al., "Induction of Endogenous Genes following Infection of Human Endothelial Cells with an E1-E+ Adenovirus Gene Transfer Vector," Journal of Virology, p. 10183-10190, vol. 73, No. 12 (Dec. 1999).
Seandel, M. et al., "Generation of a functional and durable vascular niche by the adenoviral E40RF1 gene", PNAS, v105(8), pp. 19288-19293 (Dec. 9, 2008).
Seghezzi, G. et al., "Fibroblast Growth Factor-2 (FGF-2) Induces Vascular Endothelial Growth Factor (VEGF) Expression in the Endothelial Cells of Forming Capillaries: An Autocrine Mechanism Contributing to Angiogenesis," The Journal of Cell Biology, vol. 141, No. 7, 659-1673 (Jun. 29, 1998).
Sheikh, F. et al., "Overexpression of FGF-2 increases cardiac myocyte viability after injury in isolated mouse hearts," Am J Physio Heart Gire Physiol, 280: H1039-H1050 (2001).
Shen, Q. et al., "Endothelial Cells Stimulate Self-Renewal and Expand Neurogenesis of Neural Stem Cells," Science 304, 1338-1340 (2004).
Shoji, Y. et al., "Current Status of Delivery Systems to Improve Target Efficacy of Oligonucleotides", Current Pharmaceutical Design, 2004, 10, 785-796 (2004).
Somanath, P.R. et al., "Akt1 Signaling Regulates Integrin Activation, Matrix Recognition, and Fibronectin Assembly," The Journal of Biological Chemistry, vol. 282, No. 31, pp. 22964-22976, (Aug. 3, 2007).
Songyang, Z. et al., "Recognition of Unique Carboxyl-Terminal Motifs by Distinct PDZ Domains," Science 275, 73 (1997).
Tan, P.H. et al. "Effect of Vectors on Human Endothelial Cell Signal Transduction", Arterioscler Thromb Vase Biol. 2006; 26:462-467 (Mar. 2006).
Tauber, B. et al., "Adenovirus early E4 genes in viral oncogenesis," Oncogene, 20, 7847-7854 (2001).
Toyofuku, T. et al., "Direct Association of the Gap Junction Protein Connexin-43 with Z0-1 in Cardiac Myocytes," The Journal of Biological Chemistry, vol. 273, No. 21, Issue of May 22, pp. 12725-12731 (1998).
Vandennoere, F. et al. "The antiapoptotic effect of fibroblast growth factor-2 is mediated through nuclear factor-KB activation induced via interaction between Akt and IKB kinase-f3 in breast cancer cells," Oncogene, 24, pp. 5482-5491 (2005).
Veikkola, T. et al., "Regulation of Angiogenesis via Vascular Endothelial Growth Receptors," Cancer Research 60, 203-212 (Jan. 15, 2000).
Verma, I.M. et al., "Gene therapy—promises, problems and prospects", Nature, v389, p. 239-242 (1995).
Vincent, L. et al. "Combretastatin A4 phosphate induces rapid regression of tumor neovessels and growth through interference with vascular endothelial-cadherin signaling," Journal of Clinical Investigation, vol. 115, No. 11, pp. 2992-3006 (Nov. 2005).
Wegmann, F. et al., "Endothelial adhesion molecule ESAM binds directly to the multidomain adaptor MAGI-1 and recruits it to cell contacts," Experimental Cell Research, 300, pp. 121-133 (2004).
Wang, Lisheng et al., "Derivation and Characterization of Hematopoietic Cells From Human Embryonic Stem Cells" Methods in Molecular Biology, vol. 331: 179-200, 2006 (no month listed). Humana Press, Inc., Totowa, New Jersey.
Weiss, R.S. et al., "Human Adenovirus Early Region 4 Open Reading Frame 1 Genes Encode Growth-Transforming Proteins That May Be Distantly Related to dUTP Pyrophosphatease Enzymes," Journal of Virology, pp. 1857-1870, vol. 71, No. 3 (Mar. 1997).
Weylie, B. et al., "Phospatidylinositide 3-Kinase Is Important in Late-Stage Fibroblast Growth Factor-1-Mediated Angiogenesis in vivo," J Vase Res, 43:61-69 (2006).
Xu, Chunhui et al., "Feeder-free Growth of Undifferentiated Human Embryonic Stem Cells" Technical Report. Nature Biotechnology, vol. 19: 971-974, Nature Publishing Group, Menlo Park, CA (Oct. 2001).
Yamano, S. et al., "Induction of Transformation and p53-Dependent Apoptosis by Adenovirus Type 5 E40rf6/7 cDNA," Journal of Virology, pp. 10095-10103, vol. 73, No. 12 (Dec. 1999).
Yildirim, S. et al., "Expansion of cord blood CD34p hematopoietic progenitor cells in coculture with autologous umbilical vein endothelial cells (HUVEC) is superior to cytokine-supplemented liquid culture", Bone Marrow Transplantation, 36, 71-79 (2005).
Yoshida, S. et al., "A Vasculature-Associated Niche for Undifferentiated Spermatogonia in the Mouse Testis," Science, vol. 317, pp. 1722-1726 (Sep. 21, 2007).
Zhang, B. et al., "Fibroblast Growth Factor-2 Is a Downstream Mediator of Phosphatidylinositol 3-Kinase-Akt Signaling in 14, 15-Epoxyeicosatrienoic Acid-induced Angiogenesis," The Journal of Biological Chemistry vol. 281, No. 2, pp. 905-914 (Jan. 13, 2006).
Zhang, F. et al., "Adenovirus Vector E4 Gene Regulates Connexin 40 and 43 Expression in Endothelial Cells via PKA and PI3K Signal Pathways," Circulation Research, 96(9):950-7 (May 13, 2005).
International Search Report and Written Opinion for corresponding International Patent Application No. PCT/US2004/051499.

(56) References Cited

OTHER PUBLICATIONS

Guan, K. et al., "Pluripotency of spermatogonial stem cells from adult mouse testis", Nature, vol. 440, pp. 1199-1303 (Apr. 27, 2006).

* cited by examiner

FIG. 7

```
  1 atggctgccg ctgtggaagc gctgtatgtt gttctggagc gggagggtgc
 51 tattttgcct aggcaggagg gttttcagg tgtttatgtg ttttctctc
101 ctattaattt tgttatacct cctatggggg ctgtaatgtt gtctctacgc
151 ctgcgggtat gtattccccc gggctatttc ggtcgctttt tagcactgac
201 cgatgtgaat caacctgatg tgtttaccga gtcttacatt atgactccgg
251 acatgaccga ggagctgtcg gtggtgcttt ttaatcacgg tgaccagttt
301 ttttacggtc acgccggcat ggccgtagtc cgtcttatgc ttataagggt
351 tgttttcct gttgtaagac aggcttctaa tgtttaa
```

*Common vascular genes that maintain their expression in naïve and E4ORF1⁺ PECs*

Pro-angiogenic growth factors
Basic Fibroblast Growth Factor (FGF-2)
Fibroblast Growth Factor Receptor-1 (FGF-R1)

Vascular Endothelial Growth Factor-A (VEGF-A)
Vascular Endothelial Growth Factor-C (VEGF-C)
Vascular Endothelial Growth Factor Receptor-1 (VEGF-R1)
Vascular Endothelial Growth Factor Receptor-2 (VEGF-R2)
Vascular Endothelial Growth Factor Receptor-3 (VEGF-R3)
Tie-2, Tie-1

Adhesion molecules
Vascular Endothelial Cell adhesion Moelcule (VE-Cadherin)
Intercellular Cell Adhesion Molecule (ICAM-1, ICAM2, ICAM3)
Vascular Cell Adhesion Molecule (VCAM1, VCAM2)
Endothelial selectin (E-selectin)
N-Cadherin
CD34
CD31

Extracellular Matrix protein and proteases
MMP-1, MMP-2, MMP-9, MMP-11, MMP-13, MMP-14, MMP-24, TIMP-2, TIMP-3
Collagen Type 1, alpha 2
Collagen type IV
Collagen Type XVIII
Fibronectin
SPARC/Osteonectin
Lipocalcin

---

*Vascular genes that are not expressed by either naïve or E4ORF1⁺ PECs\**

Pro-angiogenic growth factors
Fibroblast Growth Factor Receptor-2 (FGF-R2)
Fibroblast Growth Factor Receptor-3 (FGF-R3)
Fibroblast Growth Factor Receptor-4 (FGF-R4)

\* These genes were scored as "Absent" based on the analyses of the normalized data using Affimetrix Algorithm platform.

```
                          SEQUENCE LISTING

<160> NUMBER OF SEQ ID NOS: 4

<210> SEQ ID NO 1
<211> LENGTH: 386
<212> TYPE: DNA
<213> ORGANISM: Human adenovirus type 5

<400> SEQUENCE: 1
atggctgccg ctgtggaagc gctgtatgtt gttctggagc gggagggtgc tattttgcct      60
aggcaggagg gttttcagg tgtttatgtg tttttctctc ctattaattt tgttatacct     120
cctatggggg ctgtaatgtt gtctctacgc ctgcgggtat gtcttccccc gggctattcg     180
gtcgcttttt agcactgacc gatgtgaatc aacctgatgt gtttaccgag tcttacatta     240
tgcatccgga catgaccgag gagctgtcag tggtgctttt taatcacggt gaccagtttt     300
tttacggtca cgccggcatg gccgtagtcc gtcttatgct tataagggtt gttttcctg     360 ttgtaagaca ggcttctaat gtttaa                                          386

<210> SEQ ID NO 2
<211> LENGTH: 23
<212> TYPE: DNA
<213> ORGANISM: Human adenovirus type 5
<220> FEATURE:
<221> NAME/KEY: misc_feature
<222> LOCATION: (21)..(21)
<223> OTHER INFORMATION: t is dioxy
<220> FEATURE:
<221> NAME/KEY: misc_feature
<222> LOCATION: (23)..(23)
<223> OTHER INFORMATION: t is dioxy

<400> SEQUENCE: 2
gaaucaaccu gaugguguuud tdt                                             23

<210> SEQ ID NO 3
<211> LENGTH: 25
<212> TYPE: DNA
<213> ORGANISM: Human adenovirus type 5
<220> FEATURE:
<221> NAME/KEY: misc_feature
<222> LOCATION: (23)..(23)
<223> OTHER INFORMATION: t is dioxy
<220> FEATURE:
<221> NAME/KEY: misc_feature
<222> LOCATION: (25)..(25)
<223> OTHER INFORMATION: t is dioxy

<400> SEQUENCE: 3
gccaaacgcu caucagugau adtdt                                            25

<210> SEQ ID NO 4
<211> LENGTH: 29
<212> TYPE: DNA
<213> ORGANISM: Human adenovirus type 5
```

```
<220> FEATURE:
<221> NAME/KEY: misc_feature
<222> LOCATION: (27)..(27)
<223> OTHER INFORMATION: t is dioxy
<220> FEATURE:
<221> NAME/KEY: misc_feature
<222> LOCATION: (29)..(29)
<223> OTHER INFORMATION: t is dioxy

<400> SEQUENCE: 4
acccucacau caagcuacaa cuucadtdt                                      29
```

METHODS AND COMPOSITIONS FOR PROMOTING SURVIVAL AND PROLIFERATION OF ENDOTHELIAL CELLS AND STIMULATING ANGIOGENESIS

This application is a continuation of U.S. application Ser. No. 15/906,408, filed on Feb. 27, 2018, which is a continuation of U.S. application Ser. No. 13/897,829, filed on May 20, 2013, now U.S. Pat. No. 9,944,897, which is a continuation of U.S. application Ser. No. 12/523,372, filed on Dec. 22, 2009, now U.S. Pat. No. 8,465,732, which was a national stage application under 35 U.S.C. § 371 of International Application Serial No. PCT/US2008/51499, filed on Jan. 18, 2008, which claims the benefit of priority to U.S. Application Ser. No. 60/881,667, filed on Jan. 22, 2007, and U.S. Application Ser. No. 60/881,225, filed on Jan. 19, 2007. Each of the foregoing applications is incorporated by reference into the present application.

This invention was made with Government support under Grant Number HL075234 awarded by the National Institutes of Health. The Government has certain rights in the invention.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

INCORPORATION BY REFERENCE OF SEQUENCE LISTING

The Sequence Listing in an ASCII text file, named as 30171ZYX_SEQ.txt of 2 KB, created on Oct. 23, 2020, and submitted to the United States Patent and Trademark Office via EFS-Web, is incorporated herein by reference.

BACKGROUND OF THE INVENTION

The adenoviral early 4 (E4) region contains at least 6 open reading frames (E4ORFs). The entire E4 region has been shown to regulate angiogenesis and promote survival, but not proliferation, of endothelial cells (see, for example, Zhang et al. (2004), J. Biol. Chem. 279(12):11760-66). Prior to the present invention, it was not known whether all of the ORFs within the E4 region, a subset of the E4ORFs, or a single specific E4ORF, might be responsible for this activity. Use of the entire E4 region, either clinically or experimentally, to induce angiogenesis or to promote survival or proliferation of endothelial cells, may not be desirable because some of the E4ORFs can have deleterious effects. For example, the E4ORF6 gene is known to induce apoptosis (Yamano et al. (1999) J. Virol. 73:10095-103). Also, the E4ORFs are immunogenic and therefore administration of all of the E4ORFs to subjects may not be desirable. Accordingly, there was a need in the art to identify the sequences within the E4ORF region responsible for its pro-angiogenic and pro-endothelial cell survival effects. The present invention solves this problem in the art by identifying sequences within the E4ORF region that are useful for inducing angiogenesis and for promoting survival and proliferation of endothelial cells.

SUMMARY OF THE INVENTION

In one embodiment, the present invention provides a method for expanding endothelial cells (ECs) in culture, comprising obtaining a sample of primary endothelial cells, introducing into the primary endothelial cells a nucleic acid molecule comprising the adenovirus E4ORF1 gene under the control of a suitable promoter to produce E4ORF1-expressing endothelial cells, and culturing the E4ORF1-expressing endothelial cells. The step of "introducing" can be performed by any suitable method, such as by transfection or by viral-mediated transduction. In an embodiment, lentivirus-mediated transduction is used. In certain embodiments, the cells can be cultured in the absence of serum or growth factors.

In another embodiment, the present invention provides a method for inducing angiogenesis in a subject by administering endothelial cells expressing the E4ORF1 gene. For example, the present invention provides a method for inducing angiogenesis comprising obtaining a sample of primary endothelial cells, introducing into the primary endothelial cells a nucleic acid molecule comprising the adenovirus E4ORF1 gene under the control of a suitable promoter to produce E4ORF1-expressing endothelial cells, and administering the E4ORF1-expressing endothelial cells to the subject. In certain embodiments, the promoter can be an inducible promoter. The subject can be any subject in which it is desired to induce angiogenesis. In an embodiment, the subject is a mammal. In another embodiment, the subject is a human. The subject can be suffering from, or at risk of developing, an ischemic condition, such as for example, myocardial ischemia. The subject can also have a wound, such that the subject would benefit from angiogenesis during wound healing. In some embodiments, the present invention provides autologous transplantation methods whereby endothelial cells are obtained from the subject, are engineered to express the E4ORF1 gene, and are then re-administered to that same subject in order to induce angiogenesis.

In certain embodiments, the present invention also provides "gene therapy" methods. For example, the present invention provides a method for inducing angiogenesis in a subject by administering a composition comprising a nucleic acid encoding the adenovirus E4ORF1 gene under the control of a suitable promoter. Such methods can be useful for, inter alia, the treatment of ischemic conditions and for wound healing.

The present invention also provides populations and cultures of endothelial cells expressing the adenovirus E4ORF1 gene, and compositions containing such cells, such as therapeutic compositions. Endothelial cells are present in all tissues and any source of cells can be used in accordance with the present invention. Examples of endothelial cells that can be used in the present invention, include, but are not limited to, endothelial cells derived from the testis, lung, lymphatic tissue, cord blood, umbilical vein, heart, skin, liver, brain, bone, and pancreas.

In another embodiment, the present invention provides methods for targeting therapeutic agents to tumors by administering E4ORF1-expressing endothelial cells conjugated to a therapeutic agent to a subject having a tumor. Such cells can incorporate into the newly forming tumor vasculature and therefore provide a means of selectively targeting therapeutic agents to the site of the tumor. Examples of therapeutic agents that can be used include, but are not limited to, chemotherapeutic agents, toxins, and radionuclides. In certain embodiments, the therapeutic agent is conjugated to the E4ORF1-expressing endothelial cells using an antibody. The present invention also provides methods for targeting therapeutic proteins or peptides to a tumor by administering E4ORF1-expressing endothelial cells that also express a heterologous nucleotide sequence that encodes a protein or peptide that has anti-tumor activity.

In another embodiment, the present invention provides methods for producing cultures of endothelial cells suitable for use as feeder cells to support the growth of stem or progenitor cells. In one embodiment such a method comprises obtaining a sample of primary endothelial cells, introducing into the primary endothelial cells a nucleic acid molecule comprising the adenovirus E4ORF1 gene under the control of a suitable promoter, and culturing the E4ORF1-expressing endothelial cells. The present invention also provides feeder cell cultures comprising E4ORF1-expressing endothelial cells. Such cultures are particularly useful for supporting the growth of stem or progenitor cells in culture. Stem and progenitor cells that can be supported by E4ORF1-expressing endothelial feeder cells can be derived from any source from where stem and progenitor cells can be harvested.

In yet another embodiment, the present invention provides methods for producing cultures of ECs suitable for use as feeder cells to support the growth of primary cancer cells. In vitro studies on primary cancer cells have been difficult to conduct due to the inherent difficulty of primary cancer cells to grow in culture and due to their unknown growth factor requirements (Drexler et al. (2003) Leukemia 17:416-26). Accordingly, in one embodiment, E4ORF1-expressing endothelial cells are used as feeder cells to support the growth of primary cancer cells in culture in the absence of serum or growth factors. Examples of primary cancer cells that can be supported by the E4ORF1-expressing endothelial cells of the present invention include, but are not limited to, breast, colon, prostate, liver, lung, bone, epithelial, glial, neuronal, kidney, testis, ovarian, and pancreatic cells.

In another embodiment, the present invention provides methods for studying organ-specific endothelial cells and tumor-derived endothelial cells. In particular, the present invention provides a model for investigating angiogenesis and neovascularization events related to organogenesis, tumorigenesis, and metastasis in serum-free, cytokine-free conditions in vitro. In one embodiment, such a method provides obtaining a sample of organ-specific endothelial cells, introducing into the organ-specific endothelial cells a nucleic acid molecule comprising the adenovirus E4ORF1 gene under the control of a suitable promoter, and culturing the E4ORF1-expressing organ-specific endothelial cells. In another embodiment, the method comprises introducing a nucleic acid molecule comprising the adenovirus E4ORF1 gene under the control of a suitable promoter into tumor-derived endothelial cells and culturing said tumor-derived endothelial cells. The present invention also provides for an in vivo method of investigating angiogenesis and neovascularization events related to organogenesis and tumorigenesis. Specifically, the method comprises infecting endothelial cells or tumor-derived endothelial cells with lentivirus packaged to express E4ORF1, expanding the E4ORF1-expressing endothelial or tumor-derived endothelial cells in serum-free, cytokine-free culturing media, mixing the E4ORF1-expressing endothelial or tumor-derived endothelial cells with Matrigel™, and injecting the Matrigel™-endothelial cell mixture into the flanks of mice.

The present invention further provides populations and cultures of endothelial progenitor cells (EPCs) expressing the adenovirus E4ORF1 gene and compositions containing such cells, such as therapeutic compositions. Due to their diverse differentiation potential, EPCs can be quite useful in the field of vascular regenerative therapy in a number of different tissues. Expression of E4ORF1 in EPCs can thus avoid the need to isolate and culture endothelial cells from specific tissue sources. The ability to isolate and culture EPCs is known. See, for example, Ingram et al. (2005) Blood 106:1525-31 or Ingram et al. (2004) Blood 104:2752-60.

The present invention further teaches that E4ORF1 sequences from or derived from other adenovirus types or strains can also be used to promote the survival and proliferation of ECs according to the methods and compositions disclosed herein. Because all E4ORF1 proteins possess cellular growth-transforming ability when expressed at a certain level (Tauber and Dobner (2001) Oncogene 20:7847-54; Weiss et al. (1997) J Virol 71:1857-70), their ability to promote the survival and proliferation of ECs and EPCs should be conserved as well. Accordingly, in one embodiment, ECs or EPCs expressing the E4ORF1 of human adenovirus 5 can be used as disclosed herein. In another embodiment, the E4ORF1 of human adenovirus 9 can be used. The methods and compositions described can be modified to use the E4ORF1 sequence from any adenovirus type or strain.

These and other embodiments of the invention are described further in the accompanying written description, examples, drawings, and claims.

BRIEF DESCRIPTION OF THE DRAWINGS

In FIG. 1A, human umbilical vein endothelial cells (HUVEC) monolayers were cultured in serum-free, growth factor-free medium and treated with AdE4ORF1→7 (which carries the full complement of E4 complex genes), ADE4ORF1 (which expresses only E4ORF1), AdE4ORF3,4,6,6/7 (which lacks expression of E4ORF1), AdE4ORF4 (which expresses only E4ORF4) and AdE4ORF6 (which expresses only E4ORF6). The viability of ECs was quantified 3 days after infection. Data are presented as means±S.E. from three independent experiments. *, differs from control, p<0.01. Phase-contrast microscopy depicting cell morphology (FIG. 1B). HUVEC monolayers were infected with either PBS control, Lenti-E4ORF1, or Lenti-GFP for 3 days in serum-free, growth factor-free medium (FIG. 1C). FIG. 1D is a depiction of the number of HUVECs after infection with Lenti-E4ORF1 or Lenti-GFP for the indicated time. Lymphatic endothelial cells were infected with either PBS control, Lenti-E4ORF1, or Lenti-GFP for 6 days in serum-free, growth factor-free medium (FIG. 1E). In FIG. 1F, enzymatically digested human testicular tissue and human cord blood mononuclear cells were infected with Lenti-E4ORF1 for 1 day in endothelial growth medium and subsequently expanded for several passages.

In FIG. 2A, HUVEC monolayers were infected with AdE4ORF3,4,6,6/7 at 20 MOI, AdE4ORF1 at 20 MOI, and AdE4 vectors at 100 MOI in serum-free, growth factor-free medium for 48 hours. The cell lysates were then analyzed by immunoblot using polyclonal anti-phospho-Ser473 Akt antibody (pAkt) and total Akt antibody (Akt). In FIG. 2B, ECs were transfected with 20 nM E4ORF1 siRNA, E4ORF6 siRNA or the control fluorescence siRNA for 24 hours, then ECs were exposed to AdE4 vectors (100 m.o.i) in serum-free, growth factor-free medium for 2 days. Expression of pAkt or Akt was determined by Western blot using phospho-specific anti-phospho-Akt antibody (pAkt) or anti-total Akt antibody (Akt). ECs were infected with Lenti-E4ORF1 or Lenti-GFP for 3 days;

expression of pAkt or Akt was determined by Western blot (FIG. 2C). In FIG. 2D, ECs were infected with Lenti-E4ORF1 or Lenti-GFP as control. After 3 days, the Lenti-E4ORF1-transfected cells were incubated in the presence or absence of rapamycin (50 ng/ml) with or without LY-294002 (LY) (10 µg/ml) for 3 days in serum-free, growth factor-free medium. A viable cell count was taken using the trypan blue exclusion assay. Data are presented as means±S.E. from three independent experiments. Lenti-E4ORF1 infected-ECs were treated with medium alone or medium supplemented with 10 µM PD98059 (PD), or SB203580 (SB) for 2 days. The viability of ECs in serum-free, growth factor-free medium was quantified (FIG. 2E).

In FIG. 3A, HUVEC monolayers were infected with AdE4ORF1, AdE4ORF3,4,6,6/7 at 20 MOI, or AdE4ORF1→7, AdE4$^{Null}$ at 100 MOI in serum-free, growth factor-free medium for 48 h. The cell lysates were then analyzed by immunoblot using polyclonal anti-FGF2 antibody and anti-β-Actin antibody. FIG. 3B shows ECs infected with Lenti-E4ORF1 for 24 hours, then transfected with siRNA against FGF-2 for 48 hours. The cell lysates were then analyzed by immunoblot using polyclonal anti-FGF2 antibody and anti-β-Actin antibody. In FIG. 3C, ECs were infected with Lenti-E4ORF1 for 24 hours, then transfected with siRNA against FGF-2 for 48 hours. After three days in culture in serum-free, growth factor-free medium, the number of proliferating ECs was determined by trypan blue exclusion. FIG. 3D is a phase contrast microscopy picture of AdE4ORF1-infected ECs treated with control siRNA or FGF-2 siRNA. In FIG. 3E, Lenti-E4ORF1 infected-ECs were treated with 10 µM SU5402, a FGFR inhibitor or 10 µM SU5416, a VEGFR2 inhibitor for 48 hours in serum-free, growth factor-free medium or serum-free, FGF-2 supplemented medium. After 2 days in culture, the number of viable cells was counted. The time course of proliferation of naïve (control) and AdE4ORF1-infected ECs was assessed in serum-free, growth factor-free conditions, as well as serum-free medium supplemented with FGF-2 (5 ng/ml) and/or VEGF-A (10 ng/ml). The number of viable cells was counted every two to four days and plotted (FIG. 3F).

In FIG. 4G, abundant FGF-2 expression was present in E4ORF1-expressing human EC. In FIG. 4H, presence of anti-phospho-Akt staining in the nuclei of E4ORF1-expressing ECs was consistent with the in vitro results.

FIGS. 5A and 5B depict single confocal slices through areas containing GFP-positive vessel-like structures. FIGS. 5C, 5D and 5E depict full thickness projections through areas containing functional donor-derived human vessels. In FIGS. 5F, 5G, and 5H, HL60 tumor cells were co-inoculated with E4ORF1-expressing ECs subcutaneously and grown 21 days prior to harvest. Occasional vessel-like structures with a lumen were labeled by anti-human VE-cadherin (FIG. 5F) within the HL60 tumors that had been co-inoculated with E4ORF1-expressing ECs, although the vast majority of vessels were MECA-32 positive and of host origin (FIG. 5G). FIG. 5H shows little co-localization of mouse and human markers in chloromas but confirmed the specificity of the antibodies via confocal microscopy. In FIG. 5I, HL60 cells were cultured in serum-free, growth factor-free medium in the presence or absence of E4ORF1-expressing endothelial cells and counted.

FIG. 7 sets forth the E4ORF1 nucleotide sequence of human adenovirus 5, which was used in Example 1 (SEQ ID NO:1).

FIG. 9A demonstrates the ability of AdE4ORF1 to induce migration of endothelial cells in a wound healing assay. HUVECs were infected with AdE4ORF1 (20 MOI) for 24 hours, then the EC monolayers were wounded with a pipette chip and incubated in the serum-free, growth factor-free medium. After wounding of uninfected ECs, ECs were treated with or without FGF-2 (10 ng/ml) in serum-free, growth factor-free medium, as parallel control. ECs were photographed at 6 hours, 24 hours or 48 hours after wound healing. Each experiment was performed in triplicate and at least 3 times. FIG. 9B shows that AdE4ORF1-expressing cells support tube formation. ECs were infected with AdE4ORF3,4,6,6/7, AdE4ORF1, or PBS (control) and plated on Matrigel™-coated culture plates for 8 hours and analyzed for typical neo-angiogenic tube formation by phase-contrast microscopy. In FIG. 9C, ECs were infected with Lenti-GFP or Lenti-E4ORF1 in serum-free, growth factor-free medium for two days and observed under phase-contrast microscopy for their ability to form neo-angiogenic tubes 8 hours after plating on Matrigel™.

FIG. 10 identifies the common vascular EC markers expressed by both E4ORF1-expressing primary endothelial cells (PECs) and naïve PECs.

DETAILED DESCRIPTION

Figures 1A, 1B, 1C, 1D, 1E, 1F:
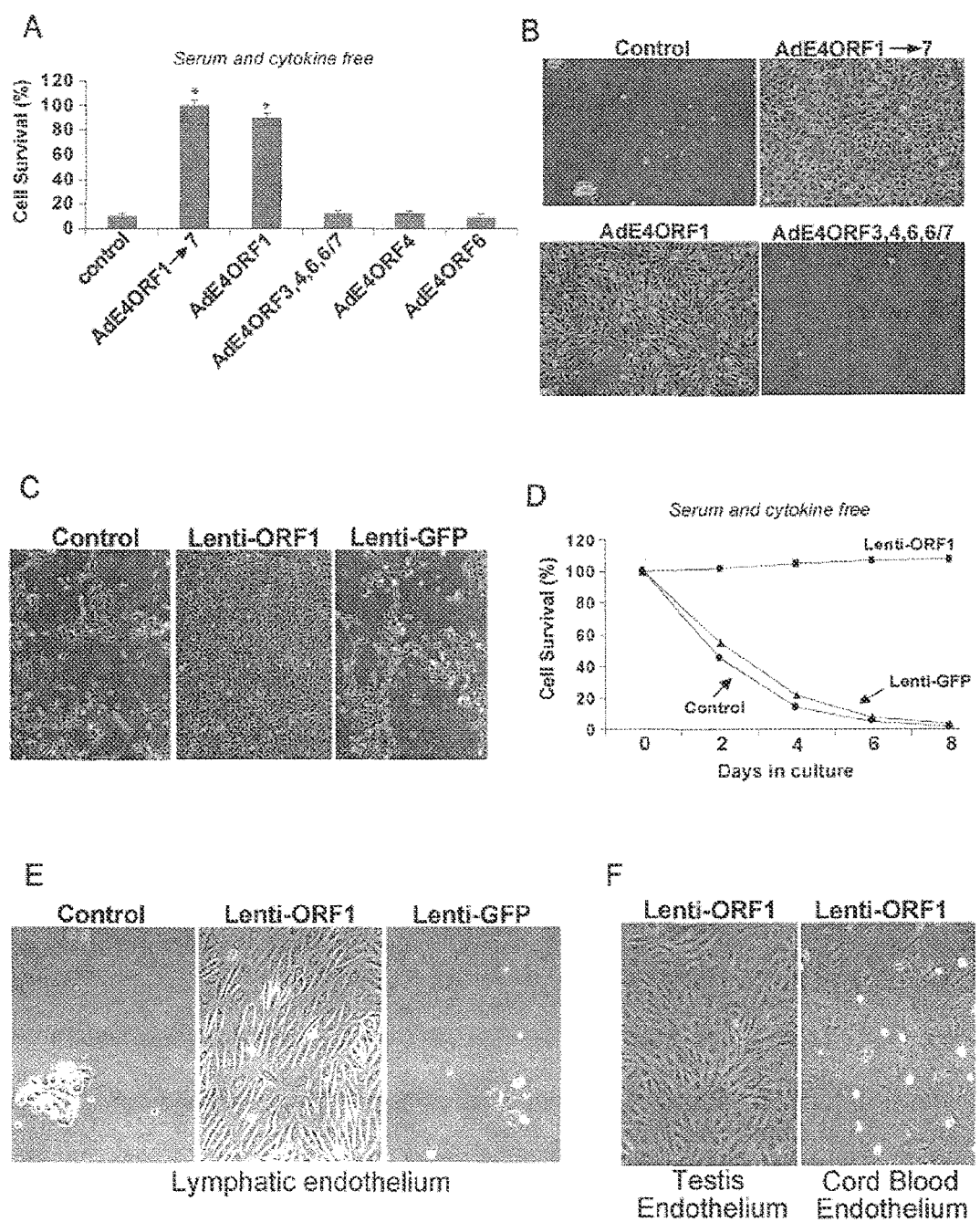
FIGS. 1A-F provide data showing that AdE4ORF1 prolongs survival of endothelial cells (ECs).

The present invention relates to the adenovirus E4ORF1 gene and to endothelial cells engineered to express the E4ORF1 gene. The present invention also relates to uses of the E4ORF1 gene, and uses of cells expressing the E4ORF1 gene, and also relates to compositions and cells comprising the E4ORF1 gene. The summary of the invention, the examples, and the claims describe some of the embodiments of the invention. Further description of certain aspects of the invention is provided below.

E4ORF1

The present invention is based, in part, upon the discovery that the E4ORF1 gene within the larger E4 region (which also encodes multiple other ORFs) has certain biological effects on endothelial cells, such as promoting survival and inducing proliferation of endothelial cells and also stimulating angiogenesis. In certain embodiments, the E4ORF1 gene used is the whole adenovirus E4ORF1 gene, or a variant, mutant or fragment thereof that has the functional properties described herein. The sequence of the human adenovirus type 5 E4 region (containing ORF1) is available on Genbank (see for example accession number D12587). In one embodiment of the invention, the E4ORF1 sequence used is that provided in FIG. 7 (SEQ ID NO: 1) or a sequence with greater than 85% sequence identity to SEQ ID NO:1. In another embodiment, the variant or mutant of the E4ORF1 sequence is a sequence with about an 85% identity to SEQ ID NO:1, or about an 88%, 89%, 90%, 91%, 92%, 93%, 94%, 95%, 96%, 97%, 98%, or 99% sequence identity to SEQ ID NO:1 that retains the ability to induce angiogenesis or promote the survival and proliferation of ECs. In another embodiment, a fragment of the E4ORF1 is a sequence which varies in length by ±30 nucleotides relative to SEQ ID NO:1, or about ±28 nucleotides, ±26 nucleotides, ±24 nucleotides, ±22 nucleotides, ±20 nucleotides, ±18 nucleotides, ±16 nucleotides, ±14 nucleotides, ±12 nucleotides, ±10 nucleotides, ±9 nucleotides, ±8 nucleotides, ±7 nucleotides, ±6 nucleotides, ±5 nucleotides, ±4 nucleotides, ±3 nucleotides, ±2 nucleotides, or ±1 nucleotides relative to SEQ ID NO:1, all of which retain the properties described herein, including, but not limited to, the ability to induce angiogenesis and the ability to promote survival and proliferation of endothelial cells.

Alternatively, the E4ORF1 sequence used can be, or can be derived from, other adenoviruses types or strains. Examples of other adenoviral E4ORF1 sequences include, but are not limited to, human adenovirus 9 (Genbank Accession No. CAI05991), human adenovirus 7 (Genbank Accession No. AAR89977), human adenovirus 46 (Genbank Accession No. AAX70946), human adenovirus 52 (Genbank Accession No. ABK35065), human adenovirus 34 (Genbank Accession No. AAW33508), human adenovirus 14 (Genbank Accession No. AAW33146), human adenovirus 50 (Genbank Accession No. AAW33554), human adenovirus 2 (Genbank Accession No. AP_000196), human adenovirus 12 (Genbank Accession No. AP_000141), human adenovirus 35 (Genbank Accession No. AP_000607), human adenovirus 7 (Genbank Accession No. AP_000570), human adenovirus 1 (Genbank Accession No. AP_000533), human adenovirus 11 (Genbank Accession No. AP_000474), and human adenovirus 3 (Genbank Accession No. ABB17792).

In some embodiments the E4ORF1 gene can be used in conjunction with one or more other genes or gene fragments from the E4 region, such as the E4ORF2, E4ORF3, E4ORF4, E4ORF5 and/or E4ORF6 genes, or variants, mutants or fragments thereof. For example, the E4ORF1 region can be used in conjunction with one or more other genes or gene fragments from the E4 region for the production of E4ORF1-expressing endothelial feeder cells. However, in other embodiments, the E4ORF1 gene is not in the context of the entire E4 region, or not in the context of the E4ORF2, E4ORF3, E4ORF4, E4ORF5 and/or E4ORF6 regions. For example, although the E4ORF1 gene can be used in a construct (such as a viral vector) that contains other genes or other coding regions (such as marker genes, antibiotic resistance genes, and the like), in certain embodiments, the E4ORF1 gene is not used in a construct that contains the entire E4 region or that contains other ORFs from the E4 region, such as E4ORF2, E4ORF3, E4ORF4, E4ORF5 and/or E4ORF6.

The E4ORF1 gene can be used in constructs that contain various other genes or coding regions, depending on the desired use. For example, the E4ORF1 gene can be used in conjunction with antibiotic resistance genes, reporter genes or expression tags (such as, for example, GFP), or any other genes that might be desirable to express in endothelial cells. The E4ORF1 gene can also be expressed as part of a fusion protein. The E4ORF1 gene can also be used in conjunction with any desired gene, coding region, or indeed non-coding regions, that may be present in the expression construct or viral vector used, or any other desired gene, coding region, or non-coding regions that is desired.

The E4ORF1 gene can be under the control of a promoter to allow for expression. Any promoter able to drive expression of the E4ORF1 gene in the desired cell type can be used. Examples of suitable promoters include, but are not limited to, the CMV, SV40, RSV, HIV-Ltr, and MML promoters. The promoter can also be a promoter from the adenovirus genome, or a variant thereof. For example, the promoter can be the promoter used to drive expression of E4ORF1 in an adenovirus.

In some embodiments, the E4ORF1 gene can be placed under the control of an inducible promoter, so that expression of the E4ORF1 gene can be turned on or off as desired. Any suitable inducible expression system can be used, such as for example, a tetracycline inducible expression system or a hormone inducible expression system. This can be useful for in vivo applications. For example, the E4ORF1 gene can be expressed while it is needed to promote angiogenesis and then switched off when there has been sufficient angiogenesis for the desired outcome, for example when there has been sufficient angiogenesis to treat an ischemic condition or heal a wound. The ability to turn off expression of the E4ORF1 gene would be useful for ensuring that there is not an excessive amount of angiogenesis or an excessive amount of endothelial cell proliferation in vivo.

Any suitable means of transfecting or transducing endothelial cells with the E4ORF1 gene can be used. For example, the E4ORF1 gene can be transfected into cells using standard methods known in the art, including, but not limited to, liposome-mediated transfection, polybrene-mediated transfection, DEAE dextran-mediated transfection, electroporation, calcium phosphate precipitation, microinjection, or micro-particle bombardment. Similarly, the E4ORF1 gene can be delivered to endothelial cells using a viral delivery system such as lentivirus, adenovirus, retrovirus, adeno-associated virus or herpesvirus delivery system. In an embodiment, the E4ORF1 gene is delivered to endothelial cells using a lentiviral gene delivery system.

The present invention also provides vectors, including expression vectors and viral vectors, which contain the E4ORF1 sequence, preferably unaccompanied by other adenovirus E4ORFs such as E4ORFs 2-6. In other embodiments, the present invention provides a lentivirus vector comprising the E4ORF1 sequence, preferably unaccompanied by other adenovirus E4ORFs such as E4ORFs 2-6. In another embodiment, the E4ORF1 sequence used in the vector is SEQ ID NO:1, or any variant, mutant or fragment thereof that retains the properties described herein, including, but not limited to, the ability to induce angiogenesis and the ability to promote survival and proliferation of endothelial cells. Such vectors can be useful for, inter alia, transfecting or transducing endothelial cells in vitro or in vivo.

Subjects

As used herein, the term "subject" is used to refer to any animal or human. In one embodiment, the subject is a mammal selected from the group consisting of primates (such as humans and monkeys), rodents, (such as mice, rats and rabbits), ovine species (such as sheep and goats), bovine species (such as cows), porcine species, equine species, feline species and canine species. Another embodiment of the invention is where the subject is a human. In certain embodiments the subject is suffering from, or at risk of developing an ischemic condition, such as myocardial ischemia, or some other condition that would benefit from or be alleviated by increased angiogenesis, for example wound healing.

Methods of Culturing and Preserving E4ORF1-Expressing Endothelial Cells

The present invention provides methods for culturing E4ORF1-expressing endothelial cells. Once endothelial cells have been transfected or transformed with the E4ORF1 gene, the cells have increased proliferative capacity, increased survival capacity and reduced senescence. Thus, the E4ORF1-expressing cells are suitable for long-term culture and expansion. The cell cultures can also be cryopreserved. One of skill in the art can readily culture and cryopreserve the E4ORF1-expressing endothelial cells of the invention using methods known to those skilled in the art, such as the methods described in Culture of Animal Cells: A Manual of Basic Technique, 4th Edition (2000) by R. Ian Freshney ("Freshney"), the contents of which are hereby incorporated by reference, and also using the methods described in the Examples.

Feeder Cells Expressing E4ORF1

Stem and progenitor cells are notoriously difficult to maintain and grow in culture. Many such cells must be cultured with a "feeder cell" layer or grown in medium conditioned by such feeder cells. However, finding a suitable source of feeder cells that will support stem cell growth, that are free from contamination, and which can be propagated under conditions that are also suitable for propagation of stem cells, is difficult. For example, in many situations primary cultures of cells, such as primary cultures of endothelial cells are used as feeder cells. However, feeder layers of primary cells, such as endothelial cells, often require the presence of serum or growth factors for maintenance. This can be problematic, as many stem cells cannot tolerate the presence of serum or certain growth factors because, for example, stem cells will differentiate in the presence of such factors. Also, many primary cell types used as feeders are not proliferative, or have low proliferative capacity, meaning that new primary cultures need to be generated frequently. This is time consuming and also leads to problems of inconsistency between batches of feeder cells. It would be desirable to have a source of feeder cells that support stem and progenitor cell growth and that are proliferative, have minimal requirements in terms of serum and growth factors, and which can be used reliably as a consistent and reproducible source of feeder cells.

E4ORF1-expressing endothelial cells of this invention are particularly useful as feeder cells for use in methods for culturing stem cells. Data provided in Example 2 illustrates the suitability of these cells as feeders to support the growth of stem cells, in particular hematopoietic stem cells and progenitor cells. The E4ORF1-expressing endothelial cells of the invention can also be useful as feeder cells for other types of stem or progenitor cells, including, but not limited to, embryonic stem cells and stem cells derived from any fetal or adult tissues such as hematopoietic stem cells, neural stem cells, skin stem cells, spermatogonial stem cells, gut stem cells, cancer stem cells and the like.

The E4ORF1-expressing cells of the invention can be plated in a layer on the surface of a culture vessel and stem cells or progenitor cells, or cell populations believed to contain stem or progenitor cells can be plated on top of the E4ORF1-expressing "feeder layer." The E4ORF1-expressing feeder cells can also be used as a source of conditioned medium for the culture of stem or progenitor cells, or can be used in conjunction with other feeder cell/stem cell culture techniques known and used in the art. The invention further provides for a composition which comprises conditioned media obtained from culturing the E4ORF1-expressing cells of the present invention.

For similar reasons as stem and progenitor cells, primary cancer cells are also notoriously difficult to grow and maintain in culture without immortalization. Accordingly, it would be desirable to have a source of feeder cells that support primary cancer cell growth, have minimal requirements in terms of serum and growth factors, and which can be used reliably as a consistent and reproducible source of feeder cells. The E4ORF1-expressing endothelial cells of the present invention can also be used as feeder cells for use in methods for culturing primary cancer cells. The E4ORF1-expressing cells of the invention can be plated in a layer on the surface of a culture vessel and primary cancer cells can be plated on top of the E4ORF1-expressing "feeder layer." The E4ORF1-expressing feeder cells can also be used as a source of conditioned medium for the culture of primary cancer cells, or can be used in conjunction with other feeder cell/cancer cell culture techniques known and used in the art. The invention further provides for a composition which comprises conditioned media obtained from culturing the E4ORF1-expressing cells of the present invention.

Therapeutic Compositions Comprising E4ORF1-Expressing Endothelial Cells

Several embodiments of the invention involve therapeutic compositions comprising E4ORF1-expressing endothelial cells. These compositions comprise a preparation of E4ORF1-expressing endothelial cells, as described above, and a carrier solution suitable for administration to living subjects, such as humans. In one embodiment, the carrier solution is a physiological saline solution. Other therapeutically acceptable agents can be included if desired. One of ordinary skill in the art can readily select suitable agents to be included in the therapeutic compositions depending on the desired outcome.

Methods of Treatment Using E4ORF1-Expressing Endothelial Cells

The present invention also provides various methods for inducing angiogenesis in subjects, and methods for treating conditions such as ischemic conditions, by administering the E4ORF1-expressing endothelial cells of the invention to the subject. One of ordinary skill in the art can readily perform such treatment methods by preparing a therapeutic composition containing E4ORF1-expressing endothelial cells, and administering the therapeutic composition to a suitable subject.

The cells can be administered to subjects using any suitable means known in the art. For example, the cells can be administered by injection or infusion into the blood stream at a location peripheral to the site where the cells are needed, or by injection or infusion into the blood stream in the vicinity of the region where the cells are needed, or by direct infusion or injection into tissue, either at the site where the cells are needed, or in the vicinity of the site where the cells are needed, or at a peripheral location. In the case of treatment of myocardial ischemia, the cells are administered directly to, or in the vicinity of, the heart. In the case of treatment of wounds, the cells are administered directly into, or in the vicinity of, the site of the wound, for example the skin in the case of a skin wound. The cells can be administered in a single dose or in multiple doses. The skilled artisan will be able to select a suitable method of administration according to the desired use.

The present invention teaches that primary or tumor-derived endothelial cells expressing the adenoviral E4ORF1 gene are angiogenic even in the absence of serum or growth factors. In addition, the present invention also teaches that expression of E4ORF1 induces FGF-2 expression. Accordingly, the cells of the present invention can be used to produce FGF-2 where FGF-2 is needed, without introducing the E4ORF1-expressing endothelial cells which can undergo angiogenesis where angiogenesis is not wanted. Thus, another embodiment entails administering E4ORF1-expressing endothelial cells in an environment (such as within a matrix, a device, a sheath or artificial layer, or within a barrier) wherein the E4ORF1-expressing endothelial cells are immobilized and cannot migrate, while allowing FGF-2 to escape and act upon cells needing FGF-2. In another embodiment of the invention, various growth or inhibitory factors secreted by primary endothelial cells, tumor-derived endothelial cells or endothelial progenitor cells can be used to localize delivery of these growth or inhibitory factors. Examples of growth or inhibitory factors secreted by these cells include, but are not limited to, FGFs, PDGF, insulin, erythropoietin, VEGF, TGF-β, G-CSF, GM-CSF, NGF, EGF, or LIF. For example, one of ordinary skill in the art can envision microencapsulating E4ORF1-expressing endothelial cells to achieve this purpose. Alternatively, a dialysis bag can be used. In any case, one of ordinary skill in the art can readily identify and employ methods well-known in the art that allow for the growth factors to be secreted while retaining the cells.

Methods of Drug Targeting

In certain embodiments, the present invention provides a method of targeting certain agents to tumors in subjects by administering to the subject E4ORF1-expressing endothelial cells that have been engineered for delivery of such agents. Because tumors frequently stimulate the in-growth of new blood vessels into the tumor (stimulate tumor angiogenesis), E4ORF1-expressing endothelial cells delivered to a subject can contribute to the new tumor vasculature. Thus, the cells can be used to deliver agents directly to a tumor site. Examples of agents that can be targeted to tumors using E4ORF1-expressing endothelial cells include, but are not limited to, cytotoxic drugs, other toxins, prodrugs, radionuclides, and gene expression products. For example, E4ORF1-expressing endothelial cells can be engineered such that they also express a protein having anti-tumor activity, or such that they secrete, release, or are coated with a toxic agent such as a chemotherapeutic agent or radionuclide. For example, radionuclide drugs or chemotherapeutic drugs can be conjugated to an antibody that binds to the surface of the E4ORF1-expressing endothelial cells and thereby used to deliver the radionuclides or chemotherapeutic drugs to a tumor. Tumors can also be targeted using E4ORF1-expressing endothelial cells engineered to secrete a prodrug-activating enzyme. After administration of the non-toxic prodrug, the E4ORF1-expressing ECs that also expressing the prodrug enzyme can convert the prodrug into its toxic form in these cells.

These and other embodiments of the invention are further described in the following non-limiting examples.

EXAMPLES

Example 1

Effects of Adenovirus E4ORF1 Gene on Endothelial Cells and on Angiogenesis

The adenoviral early 4 region (E4) contains at least 6 open reading frames (E4ORFs) and has been shown to promote survival of endothelial cells (ECs) and regulate angiogenesis. This invention provides that adenoviral vectors expressing E4ORF1 (AdE4ORF1), but not vectors with an E4ORF1 deletion (e.g., AdE4ORF1$^{null}$, AdE4ORF4 or AdE4ORF6), promoted EC survival in the absence of serum and pro-angiogenic growth factors. E4ORF1 expression using a lentiviral vector has a similar effect. The knockdown of E4ORF1 by siRNA targeted against E4ORF1 mRNA suppressed survival of ECs infected with either AdE4ORF1 or vectors expressing the full complement of adenoviral E4 (AdE4ORF 1→7). This invention provides that AdE4ORF1 and Lenti-E4ORF1 induced Akt activation via Ser473 phosphorylation and increased FGF-2 synthesis in ECs. Knocking down FGF-2 expression by siRNA abrogated the E4ORF1 EC survival effect.

Furthermore, the migration and capillary-tube formation was significantly enhanced in AdE4ORF1-infected ECs. Subcutaneous administration of Lenti-E4ORF1-infected ECs in mice induced neovascularization. These results indicate that the adenoviral E4ORF1 gene product exerts a pro-angiogenic effect by promoting survival and migratory potential of endothelial cells, and can explain the vascular toxicity observed during gene therapy clinical trials.

The gene products encoded by the early region 4 of adenovirus vectors (AdE4) not only code for key proteins essential for virus replication but also appear to be involved in the regulation of transcription, post-translational modifications, cell cycle, apoptosis, DNA repair and cell signaling (Tauber and Dobner (2001) *Oncogene* 20(54):7847-54; Leppard (1997) *J Gen Virol* 78 (Pt 9):2131-8). AdE4 promotes angiogenesis by modulating the migration, apoptosis and inflammatory potential of endothelial cells (Ramalingam et al. (1999) *Blood* 93(9):2936-44; Rafii et al. (2001) *Circ Res* 88(9):903-10; Zhang et al. (2004) *J Biol Chem* 279(12): 11760-66; Zhang et al. (2005) *Circ Res* 96(9):950-7). AdE4 promotes EC survival via regulation of several key intracellular signaling molecules, by increasing Src kinase and phosphatidylinositol 3-kinase (PI3K) phosphorylation and the Bcl2/Bax ratio, as well as reducing caspase-3 activity (Ramalingam et al. (1999) *Blood* 93(9):2936-44; Zhang et al. (2004) *J Biol Chem* 279(12):11760-66). AdE4 also regulates the gene expression of connexins 40 and 43 in ECs and mouse heart tissue (Zhang et al. (2005) *Circ Res* 96(9):950-7). However, the identity of genes transcribed by AdE4 that regulates angiogenesis is not known.

AdE4 mRNA contains at least six open reading frames (E4ORFs), suggesting that E4 encodes at least six gene products (Leppard (1997) *J Gen Virol* 78 (Pt 9):2131-8); Bridge and Ketner (1989) *J Virol* 63(2):631-8). Among the known E4ORF genes, E4ORF1 has been shown to activate several signaling pathways that support cell survival. For example, E4ORF1 has been shown to activate PI3K through a novel PDZ protein-dependent mechanism of action (Frese et al. (2003) *Oncogene* 22(5):710-21). In addition, E4ORF1 expression mimics growth factor signaling via mTOR by activating PI3K (O'Shea et al. (2005) *EMBO J* 24(6):1211-21). Therefore, E4ORF1 expressed in a vector can support angiogenesis.

The present invention provides that infection by adenoviral vectors expressing E4ORF1 alone (AdE4ORF1) is sufficient to mimic the effects of vectors expressing the full complement of adenoviral E4 (AdE4ORF1→7) on ECs, prolonging cell survival in serum-free and growth factor-free culture conditions. Specifically, AdE4ORF1 promotes angiogenesis via activation of PI3K-Akt signaling and induces fibroblast growth factor-2 (FGF-2) production, thereby enhancing the survival and migratory capacity of the ECs. The invention provides that expression of the AdE4ORF1 gene product is essential for the AdE4-mediated pro-survival and pro-angiogenic effects on ECs.

Cell culture. Human umbilical vein endothelial cells (HUVECs) were isolated and cultured in EC medium (M199 medium containing 10% (v/v) fetal bovine serum, 20 µg/ml EC growth factor, 20 units/ml heparin, 100 µg/ml penicillin and 100 µg/ml streptomycin) in a humidified incubator at 37° C. with air/5% $CO_2$ (Zhang et al. (2004) *J Biol Chem* 279(12):11760-66). HUVEC monolayers between passages 2 to 4 were used in these studies. Cell viability was assayed by the trypan blue exclusion method, indicating that fewer than 5% of the cells took up the dye both before and after the infection of adenoviral vectors.

Construction of adenoviral vectors. The adenoviral vectors used included: AdE4ORF1→7, derived from adenovirus type 5, which expresses E4ORFs from E4ORF1 to E4ORF6/7 but has deletions of the E3 and E1 gene complexes with no transgene in the expression cassette (Hersh et al. (1995) *Gene Ther* 2(2):124-31); AdE4ORF6 (expresses only E4ORF6 from the E4 promoter—all other E4ORFs were deleted); AdE4ORF1, which carries only E4ORF1 and has deletions of E4ORFs 2, 3, 4, 5, 6/7; AdE4ORF3,4,6,6/7, which carries E4ORFs 3, 4, 6 and 6/7, and has deletions of E4ORF1 and E4ORF2; AdE4ORF4 which carries only E4ORF4 and deletions of all other E4ORFs, and AdE4$^{null}$ which lacks the expression of all E4ORFs, as previously described (Querido et al. (1997) *J Virol* 71(5):3788-3798; Bridge and Ketner (1990) *Virology* 174(2):345-353). The AdE4ORF4, AdE4ORF3,4,6,6/7, and AdE4ORF1 virus vectors were propagated on W162, a Vero-derived, E4-complementing cell line. AdE4ORF1→7 and AdE4ORF6 were amplified in 293 cells and purified by cesium chloride centrifugation and dialysis as described in Crystal et al. (1994) *Nat Genet* 8(1):42-51. All adenoviral vectors had a particle/pfu ratio of approximately 100.

LentiE4ORF1—Generation of Lentivirus and Infection. E4ORF1 gene was cloned into the Lentivirus vector. Lentiviruses were generated by co-transfecting 15 µg of lentiviral vector, 3 µg of pENV/VSV-G, 5 µg of pRRE and 2.5 µg of pRSV-REV (see Dull et al. (1998) *J Virol* 72:8462-71) in 293T cells (passage 8-10, subconfluent) by calcium precipitation method. Medium was changed 24 hours after transfection, and supernatants were collected 40 hours and 64 hours after transfection. Supernatants were immediately sterile-filtered using surfactant-free cellulose acetate membranes, aliquoted and stored at −80° C.

siRNA Preparation and Transfection. siRNA for adenovirus E4ORF1 (target sequence, 5'-GAAUCAACCUGAU-GUGUUU-dTdT-3') (SEQ ID NO:2) and E4ORF6 (target sequence, 5'-GCCAAACGCUCAUCAGUGAUA-dTdT-3') (SEQ ID NO:3), and FGF-2 (target sequence, 5'-ACCCU-CACAUCAAGCUACAACUUCA-dTdT-3') (SEQ ID NO:4) were designed and synthesized by Invitrogen (Stealth™ RNAi). dTdT 3' overhangs were not part of the siRNA sequence, but rather were present to facilitate RNA interference using short interfering RNA sequences. Twenty nM of siRNA preparation were transfected individually into ECs using Lipofectamine™ 2000 following Invitrogen's protocols and experiments were conducted 24 hours after transfection. The control siRNA (scrambled sequence), and siRNA against GFP, as another control, were used as the same concentrations. The transfection efficiency of each duplex siRNA (~80%) was confirmed by using Block-iT™ Fluorescent Oligo (Invitrogen).

Western Blot Analysis. Cells were lysed in RIPA buffer (50 mM Tris, 150 mM NaCl, 1% NP-40, 0.1% sodium dodecyl sulfate, and 2 µg/ml aprotinin). Insoluble debris was pelleted, and the protein concentration of the supernatant was determined with a DC protein assay kit (Bio-Rad). Fifty micrograms of each protein sample were separated on 10% SDS-PAGE gels. The protein samples were then transferred to nitrocellulose membrane. Protein expression was confirmed by immunoblotting with the following antibodies: Ser473-phospho-Akt, total Akt, FGF-2, β-actin. After incubation with the appropriate primary and horseradish peroxidase-conjugated secondary antibodies, the membranes were developed with enhanced chemiluminescence reagent (Amersham Pharmacia Biotechnology).

Wound Healing Assay. HUVECs were maintained in subconfluence in EC medium, and then infected with AdE4ORF1, AdE4ORF3,4,6,6/7, or PBS. Twenty-four hours after infection, confluent HUVEC monolayers were wounded with a pipette chip and incubated in the serum-free, growth factor-free medium (X-vivo medium) for experiments. After 24 and 48 hours, the cells that had migrated across the edge of the wound were observed under microscopic vision. Each experiment was performed in triplicate and at least 3 times.

Tube Formation Assay. The formation of vascular-like structures by HUVEC on Matrigel™ (Becton Dickinson) was semi-quantified by phase contrast microscopy. Twenty-four well culture plates were coated with Matrigel™ according to the manufacturer's instructions. HUVECs were infected with or without adenovirus, then seeded on coated plates at $5 \times 10^4$ cell/well in serum-free medium (SFM) and incubated at 37° C. for 8 hours. Uninfected HUVECs were seeded on coated plate in SFM containing VEGF-A (10 ng/ml) and FGF-2 (10 ng/ml) as a positive control.

In vivo Matrigel™ Plug Assay. To determine whether human E4ORF1-expressing endothelial cells can participate in neo-angiogenesis in vivo, these cells were inoculated with Matrigel™ plugs and/or HL60 leukemic cells. To assess angiogenesis in vivo, ECs were infected with Lenti-E4ORF1 and cultured for 7-14 days. Uninfected ECs were used as controls. Subsequently, ECs were detached using collagenase. $4 \times 10^6$ ECs per mouse were mixed with Matrigel™ (BD Biosciences, San Jose, CA). The Matrigel™-EC mixtures (400 µl) were implanted into the flanks of two groups of mice. The mice were sacrificed after 5 to 10 days for analysis, at which time the Matrigel™ plugs were photographed, removed and snap-frozen immediately in OCT (Tissue-Tek).

For functional analysis of the angiogenic potential of E4ORF1-expressing ECs in vivo, ECs were co-infected with Lenti-E4ORF1 and Lenti-GFP in 35 mm dishes and expanded. ECs infected with Lenti-GFP and passaged in parallel served as controls. Subsequently, ECs were detached using collagenase and $10\times10^6$ ECs were mixed with 200 µl Matrigel™. The Matrigel™-EC mixtures were subcutaneously injected into the flanks of NOD-SCID mice (200 µl/flank). After two weeks, the mice were anesthetized and inoculated intravenously with 100 µg of biotinylated-Ulex europaeus agglutinin-1 (UEA-1) (Sigma-Alderich, St. Louis, MO) to detect the incorporation of human ECs into vessels continuous with the mouse circulation just prior to sacrifice. After 30 minutes, the mice were further anesthetized and transcardially perfused with 15 ml of 4% paraformaldehyde/PBS after initial flushing with 20 ml PBS. The Matrigel™ plugs were dissected out, post-fixed for 2-3 hours in 4% paraformaldehyde/PBS, washed extensively, equilibrated for 48 hours in 30% sucrose, and snap-frozen in OCT. To assess for functional GFP-positive vessels, 30 micron cryosections were cut, blocked in 10% donkey serum for 30 minutes, and incubated with streptavidin-Alexa647 conjugate (Invitrogen) for 30 minutes to detect biotinylated-UEA-1 bound to functional human vasculature. Slides were washed and mounted in glycerol containing 1 µg/ml propidium iodide (Sigma Alderich) as a nuclear counterstain and examined by confocal microscopy using a Zeiss 510 Meta confocal microscope for the presence of vessels co-stained for GFP and UEA-1.

In separate groups of mice, $5\times10^6$ ECs were combined with HL60 leukemia cells. The Matrigel™-EC or Leukemia-EC mixtures were then injected subcutaneously into the flanks of the separate groups of NOD-SCID mice (400 µl/mouse). After 21 days, the mice were sacrificed and analyzed as described above.

Immunostaining. The presence of E4ORF1-expressing ECs was assessed using mouse and human antibodies. Rabbit polyclonal anti-human FGF-2 antibody (Santa Cruz Biotechnology, Santa Cruz, CA), rabbit polyclonal anti-phospho-Akt (Santa Cruz Biotechnology, Santa Cruz, CA), goat polyclonal anti-human VE-cadherin 1 antibody (R&D Systems), MECA-32 rat anti-mouse endothelial monoclonal antibody (CD Pharmingen), mouse anti-human CD34 monoclonal antibody, anti-human CD31 monoclonal antibody, and rabbit anti-human von Willebrand factor (Dako, Carpinteria, CA) were employed. After overnight incubation with the primary antibodies at 4° C., detection was performed using biotinylated donkey secondary antibodies (Jackson ImmunoResearch, West Grove, PA), followed by streptavidin-Alexa488 conjugate (Invitrogen, Carlsbad, CA). Propidium iodide (1 µg/ml) was used as a counterstain for the nuclei. For immunostaining of the Matrigel™ plugs, 7 µm cryosections were prepared and fixed with 4% paraformaldehyde (PFA) for Hematoxylin and Eosin (H&E) staining and immunohistochemistry (IHC). Incubation with primary antibody was performed as described above. Bound antigen was detected with donkey biotinylated anti-rabbit secondary antibody, followed by streptavidin-HRP (both from Jackson ImmunoResearch) and DAB or AEC.

Microarray Gene Expression Profile. Affymetrix's Human Genome U133 Plus 2.0 Array was used to analyze gene expression. Total RNA was extracted from control ECs and E4ORF1-expressing ECs using Trizol™ (Invitrogen). ECs were grown for 24 hours under serum-free, growth factor-free medium prior to RNA extraction. cDNA was synthesized from the total RNA extracted. Biotinylated cRNA was made from the cDNA by in vitro transcription using a kit (Enzo Diagnostic). Fragmented cRNA was hybridized to the gene chips, washed, and stained with streptavidin phycoethrin. The probe arrays were scanned with the Genechip System confocal scanner, data processed with Affymetrix Microarray Suite 4.0 and analysis was performed using Genespring GX (Agilent).

Adenovirus E4ORF1 Promotes Survival of Endothelial Cells

Adenovirus E4 positive vectors that express all six E4 gene products promote EC survival and prevent apoptosis even in of the absence of pro-angiogenic factors, including VEGF-A and serum (Zhang et al. (2004) *J Biol Chem* 279(12):11760-66). However, prior to this invention, it was not clear which of the six E4 open reading frame (ORF) genes of the E4 gene confers this unique pro-angiogenic phenotype to the ECs. To identify the specific adenoviral E4ORF, which selectively promotes neo-angiogenesis, ECs were infected in serum-free, growth factor-free medium with adenoviral vectors carrying various E4ORF sequence deletions, including AdE4 vectors lacking either E4ORF1, E4ORF4, E4ORF6, or a combination of E4ORF3,4,6,6/7. As shown in FIGS. 1A and B, an increase in the survival of ECs was observed in cells infected with E4ORF1, including AdE4ORF1→7, which expresses all six E4 ORFs and AdE4ORF1, which only expresses E4ORF1. In contrast, AdE4ORF3,4,6,6/7, AdE4ORF4 and AdE4ORF6 did not improve EC survival in serum-free, growth factor-free conditions. Therefore, the invention provides that among the known E4ORFs that are known to convey survival signals, E4ORF1 plays a central role in the AdE4 regulation of EC survival.

In order to rule out the possible involvement of other adenovirus genes in the E4ORF1 effect, a lentivirus specifically expressing only E4ORF1 without any other adenoviral genes was generated. ECs were infected with Lenti-GFP or Lenti-E4ORF1. Infection with the E4ORF1-lentivirus significantly increased the survival of ECs in serum-free, growth factor-free medium compared to infection with GFP-lentivirus or to non-infected (control) ECs (FIGS. 1C and D). Transfection efficiency of ECs was almost 100%, as measured by GFP expression in Lenti-GFP infected cells. A similar effect of E4ORF1-lentivirus was also seen in lymphatic endothelial cells (FIG. 1E). In summary, the E4ORF1-lentivirus replicated the AdE4ORF1 EC survival effect, including the typical cobblestone morphology of ECs grown in monolayers. These data further indicate that E4ORF1 is responsible for the pro-survival effect of AdE4 in ECs.

Figures 8A, 8B, 8C, 8D:
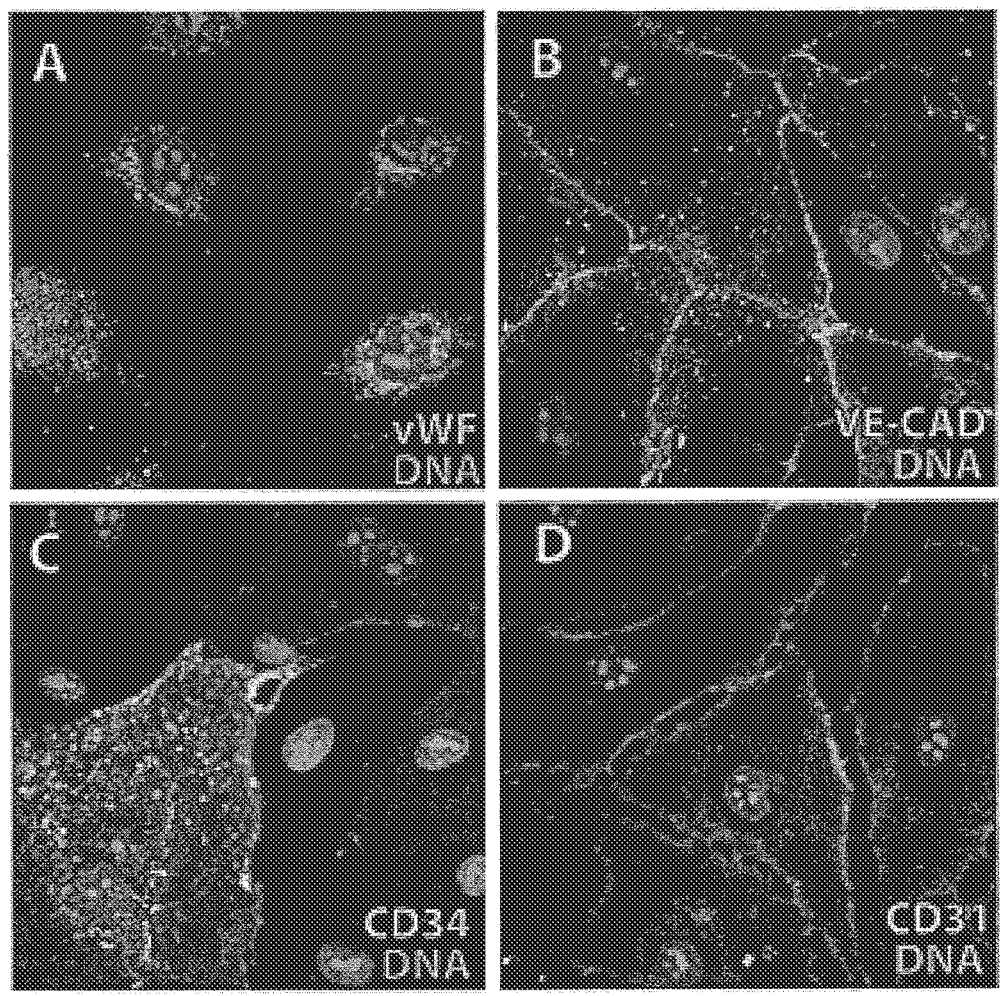
FIGS. 8A-D show that testicular cells expressing E4ORF1 characteristically expressed endothelial cell markers. Testicular biopsy tissue was enzymatically dissociated, transduced at passage zero with E4ORF1, and serially passaged and expanded using standard EC growth medium. Homogenous cells with endothelial morphology were stained with von Willebrand factor (FIG. 8A), VE-cadherin (FIG. 8B), CD34 (FIG. 8C), and CD31 (FIG. 8D) along with prodium iodide.

To further verify the ability of E4ORF1 to selectively promote the outgrowth of organ-specific endothelial cells, crude populations of enzymatically digested human testicular cells or fresh human umbilical cord blood mononuclear cells were infected with Lenti-E4ORF1. Compared with non-infected cultures, ECs infected with the E4ORF1-lentivirus supported the outgrowth of monolayers of these organ specific ECs (FIG. 1F). The ECs were highly pure, grew in a contact inhibited manner, and expressed the typical markers of the endothelium, including CD34, von Willebrand factor, VE-cadherin, and CD31 (FIG. 8). These data further supports the finding that E4ORF1 selectively confers pro-survival effects to organ-specific ECs.

E4ORF1 Activates Phosphorylation of Akt

Figures 2A, 2B, 2C, 2D, 2E:
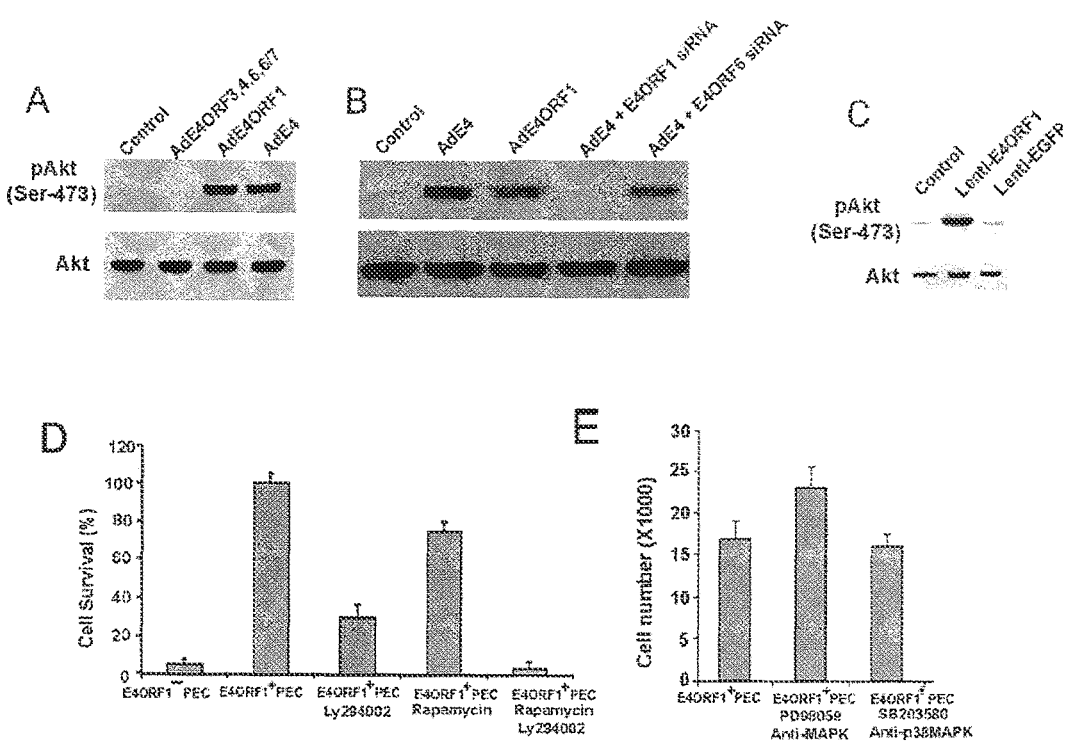
FIGS. 2A-E demonstrates that E4ORF1 activates pAkt in endothelial cells (ECs).

Phosphorylation of Akt is a key component of AdE4ORF1→7-mediated EC survival (Zhang et al. (2004) *J Biol Chem* 279(12):11760-66). To test whether E4ORF1 is responsible for the phosphorylation of Akt in AdE4ORF1→7 transduced ECs, siRNA against E4ORF1 was used to inhibit the expression of E4ORF1. Infection of the ECs with either AdE4ORF1→7 or AdE4ORF1, but not AdE4ORF3,4,6,6/7, induced phosphorylation of Akt at Ser473, with total Akt remaining constant (FIG. 2A). However, pretreatment of ECs with siRNA against E4ORF1 completely inhibited AdE4ORF1→7 virus-induced pAkt activation, as compared to the ECs transfected with either fluorescein-labeled siRNA (control) or E4ORF6 siRNA (FIG. 2B). Moreover, infection of ECs with the lentiviral E4ORF1 vector also increased Akt phosphorylation at Ser-473 (FIG. 2C) compared to control or to infection with Lenti-GFP, indicating that Akt activation is E4ORF1-specific. Infection of smooth muscle cells with lentiviral E4ORF1 had no significant effect on Akt activation, showing that E4ORF1's ability to phosphorylate Akt is specific to ECs.

To test whether AdE4ORF1 prolongs EC survival through mTOR or PI3K signaling, AdE4ORF1-infected ECs were exposed to rapamycin, an inhibitor of mTOR signaling, or to LY-294002, an inhibitor of PI3K signaling. The pro-survival effects of AdE4ORF1 were only moderately reduced by rapamycin (FIG. 2D). In comparison, LY-294002 significantly suppressed the effect of AdE4ORF1, and LY-294002 together with rapamycin completely eliminated the E4ORF1 survival effect (FIG. 2D). Together, these results indicate that E4ORF1-mediated survival, like AdE4-mediated survival, involves EC-specific Akt activation, and that the mTor-PI3K signaling pathway is also likely involved. To determine whether E4ORF1 prolonged EC survival was regulated by MAPK, E4ORF1-infected ECs were treated with MAPK inhibitors PD98059, a selective inhibitor of ERK, and SB203580, a selective inhibitor of p38-MAPK). Neither PD98059 nor SB203580 had significant effects on the survival effects of E4ORF1-expressing ECs. These results indicate the E4ORF1 survival effect involves the EC-specific Akt activation and in part is mediated through the recruitment of the PI3K-Akt-mTOR signaling pathway.

E4ORF1 Induces Expression of FGF-2

In order to identify the mechanism by which AdE4ORF1 promotes the pro-angiogenic effect on ECs, a microarray expression analysis was performed on Lenti-E4ORF1-infected ECs and compared them to the Lenti-GFP infected ECs, both grown under serum-free, growth factor-free conditions for 24 hours. The commonly known pro-angiogenic factors essential for survival and proliferation of ECs maintained their expression pattern in both E4ORF1-infected and GFP-infected ECs. Results are shown in FIG. 10. This data indicates that although naïve ECs require exogenous FGF-2 for optimal activation, E4ORF1-infected ECs requires Akt-dependent intrakine activation of the FGF-2/FGF-R1 pathway for survival.

Figures 3A, 3B, 3C, 3D, 3E, 3F:
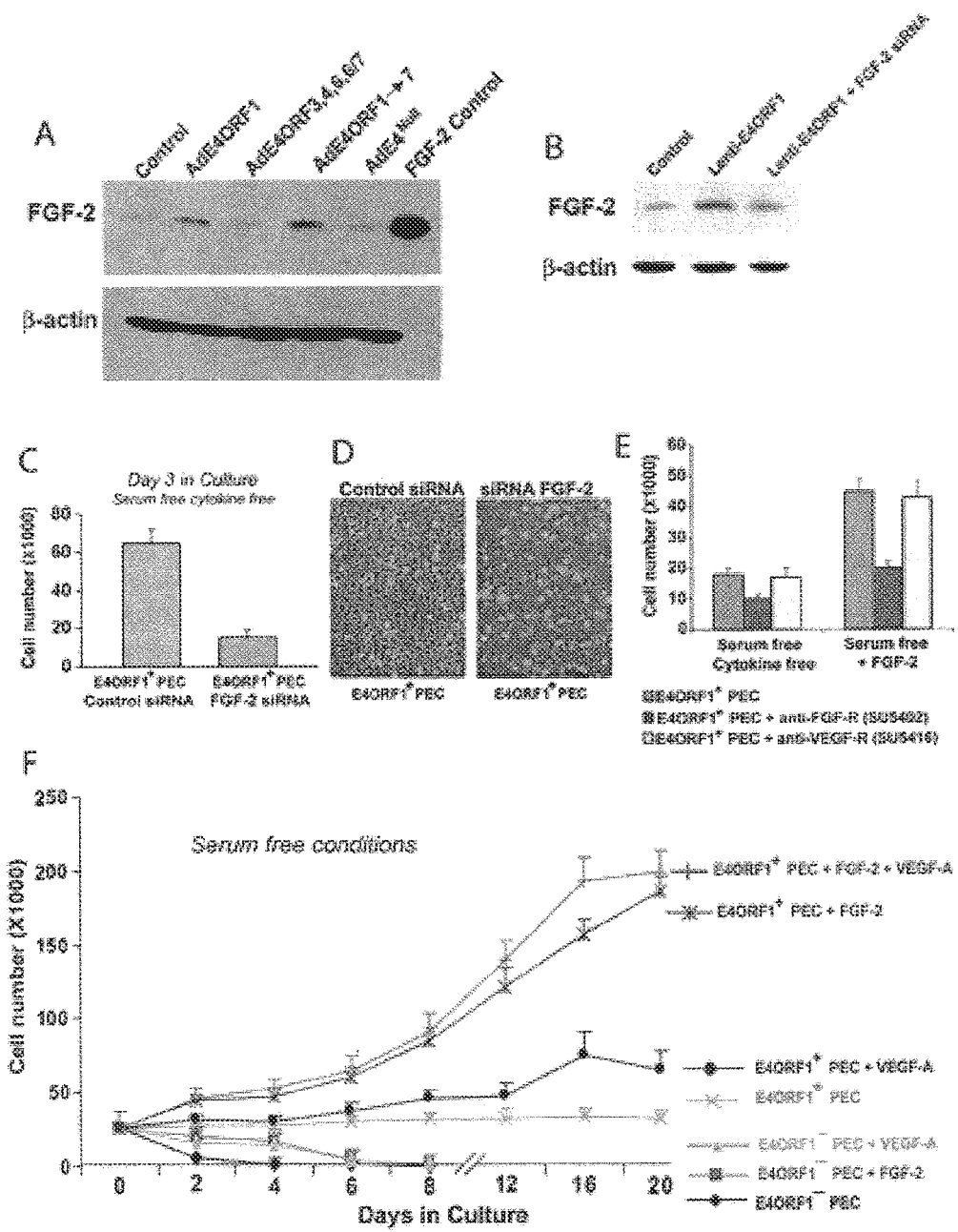
FIGS. 3A-F provide data that demonstrates that AdE4ORF1-mediated activation of the FGF-2/FGF-receptor pathway promotes the survival and proliferation of endothelial cells (ECs).

Whether AdE4ORF1→7 or AdE4ORF1 (expressing only E4ORF1) promotes EC survival via increased expression of the pro-angiogenic factor FGF-2 was next examined. As shown in FIGS. 3A and 3B, ECs infected with AdE4ORF1 or AdE4ORF1→7 significantly increased FGF-2 protein expression when compared to naïve ECs or ECs infected with adenoviral vectors lacking E4ORF1. ECs infected with Lenti-E4ORF1 also increased protein levels of FGF-2 (FIG. 3B). FGF-2 knockdown by FGF-2 siRNA blocked E4ORF1-mediated survival (FIGS. 3C and D). Diminished FGF-2 protein expression by the FGF-2 siRNA was confirmed by Western blot analysis and suppressed E4ORF1-induced FGF-2 protein expression (FIG. 3B).

In addition to the FGF-2/FGFR-1 pathway, VEGF-A/VEGF-R could also contribute to the E4ORF1-mediated survival effect seen in ECs. Although SU5402, an inhibitor of FGF-R1 tyrosine kinase activity, blocked this expansion of rFGF-2-treated E4ORF1-infected ECs, the VEGF-A receptor inhibitor SU5416 did not significantly affect the survival or proliferation of E4ORF1-expressing ECs, either in the presence or absence of FGF-2 (FIG. 3E). Taken together, this shows that E4ORF1 exerts its pro-survival effect in part through the activation of the FGF-2/FGFR-1 complex rather than the VEGF-A/VEGFR pathway.

To further attribute the pro-survival effect of E4ORF1-expressing ECs through the activation of FGFR-1, recombinant FGF-2 (rFGF-2) was added to the serum-free culture medium (FIG. 3F). In serum-free, growth factor-free medium, E4ORF1-expressing ECs survived without any proliferation, maintaining their contact-inhibited status, whereas ECs which did not express the E4ORF1 gene product rapidly underwent apoptosis. The addition of rFGF-2 to serum-free, growth factor-free cultures of E4ORF1-expressing ECs robustly increased the proliferation of ECs. rFGF-2 briefly supported the survival of ECs which did not express E4ORF1, but these cells eventually became progressively apoptotic. Addition of exogenous recombinant VEGF-A (rVEGF-A) alone or with rFGF-2-treated E4ORF1-expressing ECs had a weak effect on survival or expansion of ECs expressing E4ORF1, as compared to treatment with rFGF-2 alone. These data shows that E4ORF1-mediated upregulation of the FGF-2/FGF-receptor system plays a critical role for the E4ORF1-mediated survival of ECs, while addition of exogenous FGF-2 not only promotes survival, but also induces proliferation of E4ORF1-expressing ECs in serum-free, growth factor-free conditions.

E4ORF1 Maintains the Functional Properties of ECs

Figures 9A, 9B, 9C:
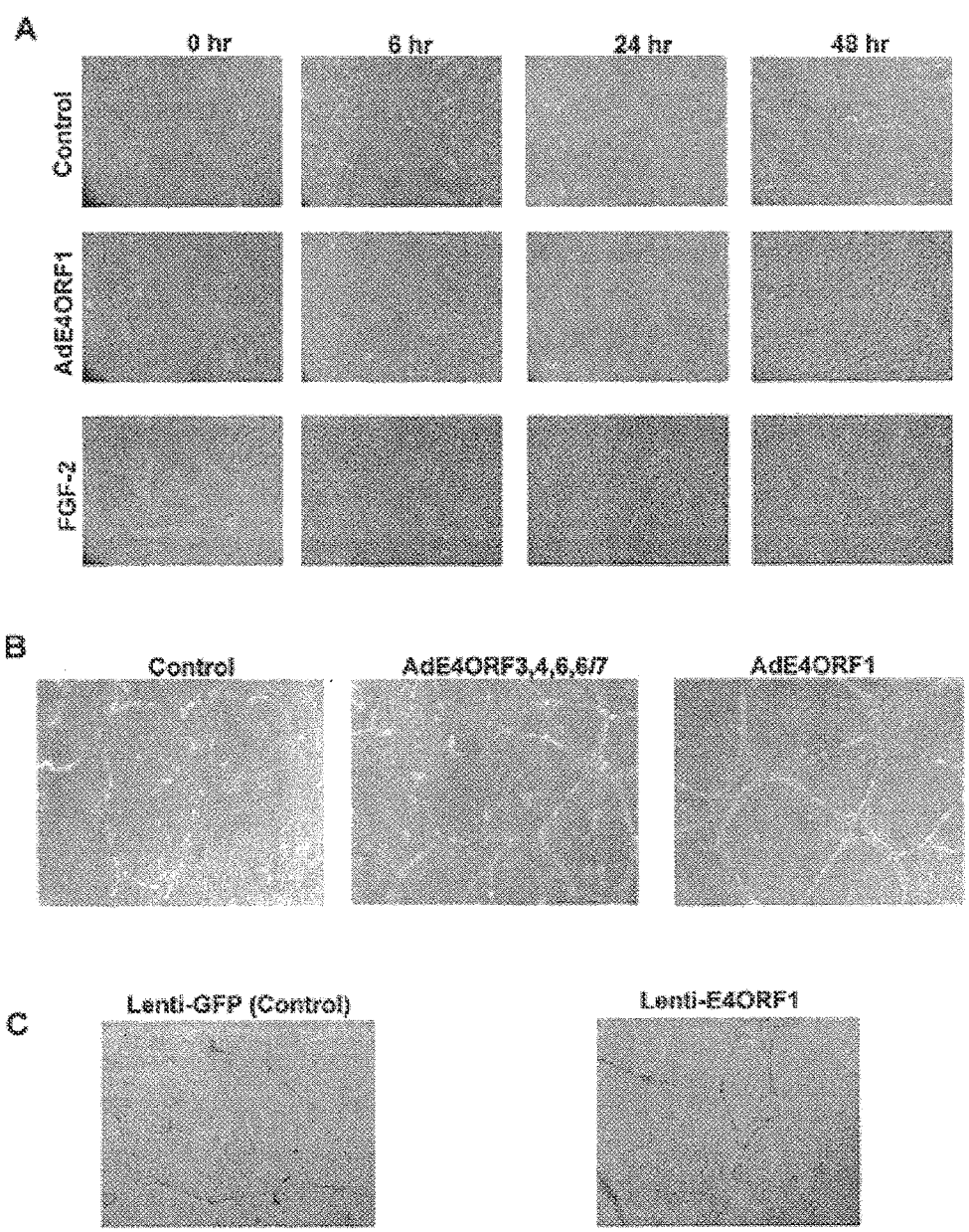
FIGS. 9A-C show that E4ORF1 stimulates migration and tube formation of ECs.

ECs have the capacity to carry out angiogenic processes in vitro, including the ability to form tubes and to migrate. Whether E4ORF1-infected ECs retain these properties was next examined. As shown in FIG. 9, infection with AdE4ORF1 enhanced the wound-induced migration of ECs in serum-free, growth factor-free medium. This effect is similar to that observed when exogenous rFGF-2 is added to ECs. In contrast, both uninfected and AdE4$^{null}$-infected ECs in serum-free, growth factor-free medium were unable to migrate, instead undergoing apoptosis. Whether E4ORF1 affects EC tube formation was investigated. ECs were infected with AdE4ORF1 or AdE4ORF3,4,6,6/7 for 24 hours before being seeded in Matrigel™. As shown in FIGS. 9B and 9C, ECs infected with AdE4ORF1 or Lenti-E4ORF1 maintained their ability to form tubes in serum-free conditions for over 2 days, whereas control ECs or AdE4ORF3, 4,6,6/7-infected ECs only maintained tube-forming activity for less than 1 day, after which there was a rapid dissociation of the tubes. These data indicate that E4ORF1-infected ECs maintain neo-angiogenic potential.

E4ORF1-Expressing ECs Rapidly Organize into Vessel-Like Structures In Vivo

Figures 4A, 4B, 4C, 4D, 4E, 4F, 4G, 4H:
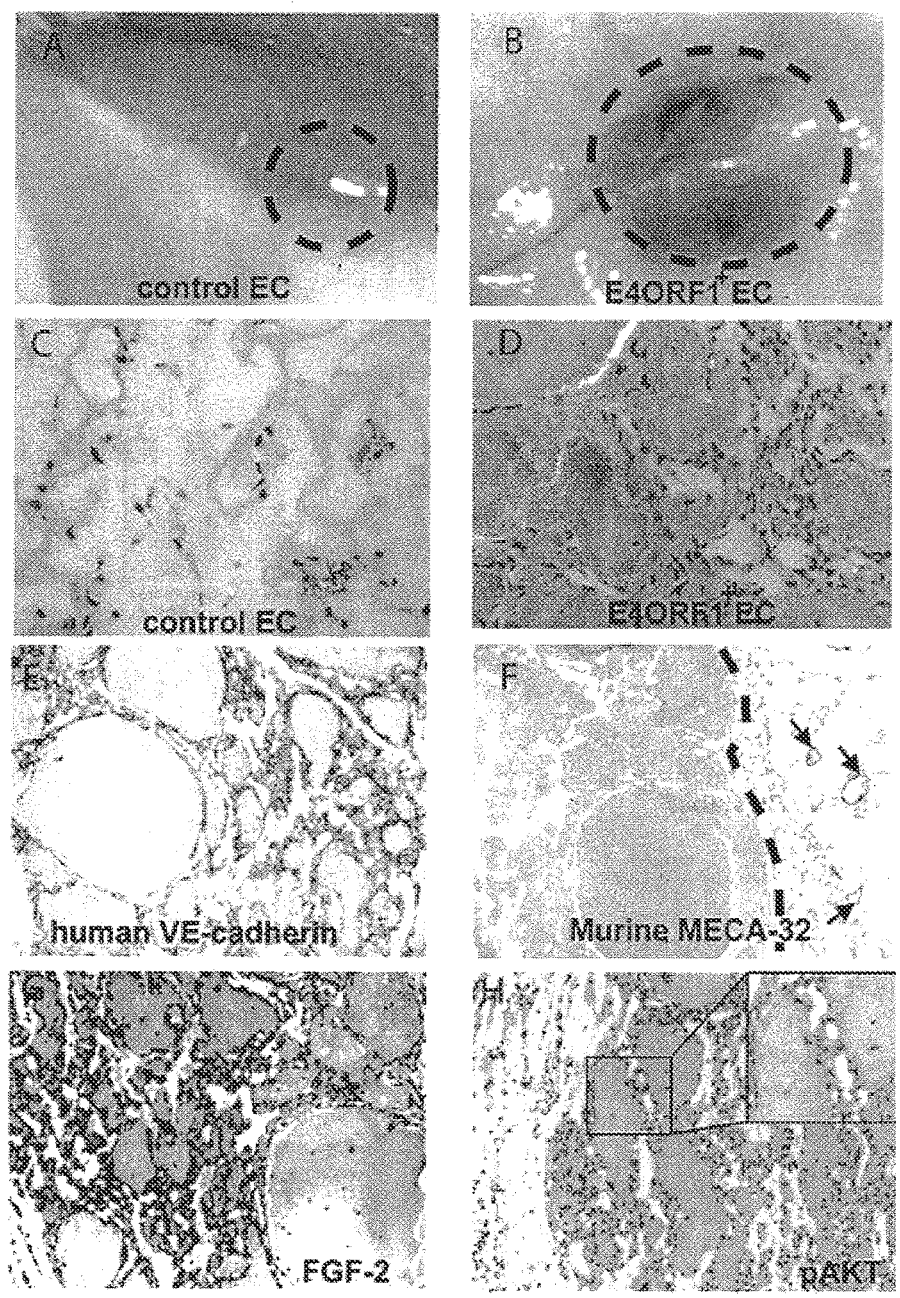
FIGS. 4A-H show in vivo survival and angiogenesis of ECs in NOD/SCID mice. Mice received subcutaneous inoculations of Matrigel™ containing either human EC alone or AdE4ORF1-expressing ECs. In the absence of E4ORF1, human ECs survived poorly after 5 days, forming barely detectable masses (FIGS. 4A and 4C), whereas ECs expressing E4ORF1 formed obvious hemorrhagic lesions, both at the gross level (FIG. 4B) or in histologic sections stained with hematoxylin and eosin (FIG. 4D) Immunohistochemistry staining for human endothelium (anti-human VE-cadherin) revealed strong staining in areas containing human ECs expressing E4ORF1 (FIG. 4E), whereas mouse endothelium (labeled with MECA-32) was detectable only adjacent to the EC masses (FIG. 4F, arrows indicate mouse vessels).

Primary human endothelial cells have limited survival and functionality in mouse xenograft angiogenesis assays (Koizumi et al. (2003) *Biochem Biophys Res Comm* 306:219-24). Based on the phenotypic changes observed in vitro in human ECs stably transduced with lenti-E4ORF1 that implied an enhanced angiogenic capability, the performance of these cells in vivo was next assessed. Whereas normal ECs were barely detectable five days after injection subcutaneously into immunocompromised mice (FIG. 4A), E4ORF1-expressing EC survived and established vascular nodules (FIG. 4B), and organized rapidly into primitive vascular-type structures (FIGS. 4C and D). These exhibited circular morphology in cross-section, with a central core of degenerating red blood cells. To distinguish human EC from host (mouse) endothelium, species-specific antibodies were employed and unequivocal labeling of nests of engrafted ECs with anti-human VE-cadherin was observed (FIG. 4E), which did not recognize adjacent mouse vessels. Conversely, labeling of mouse endothelium with MECA-32 delineated the adjacent mouse vessels surrounding but not intermingling with AdE4ORF1 ECs (FIG. 4F). Consistent with the biochemical profile of AdE4ORF1-infected ECs in vitro, robust FGF-2 expression was detected in the engrafted tissue compared to the adjacent host connective tissue (FIG. 4G). Staining of these sections with a phospho-Akt specific antibody shows that E4ORF1-expressing ECs had maintained their chronic Akt activation (FIG. 4H). These data indicate that for at least five days following Matrigel™ implantation, E4ORF1-expressing ECs retained their Akt-dependent neo-angiogenic potential, forming vascular structures without generating tumorigenic vessels.

Figures 5A, 5B, 5C, 5D, 5E:
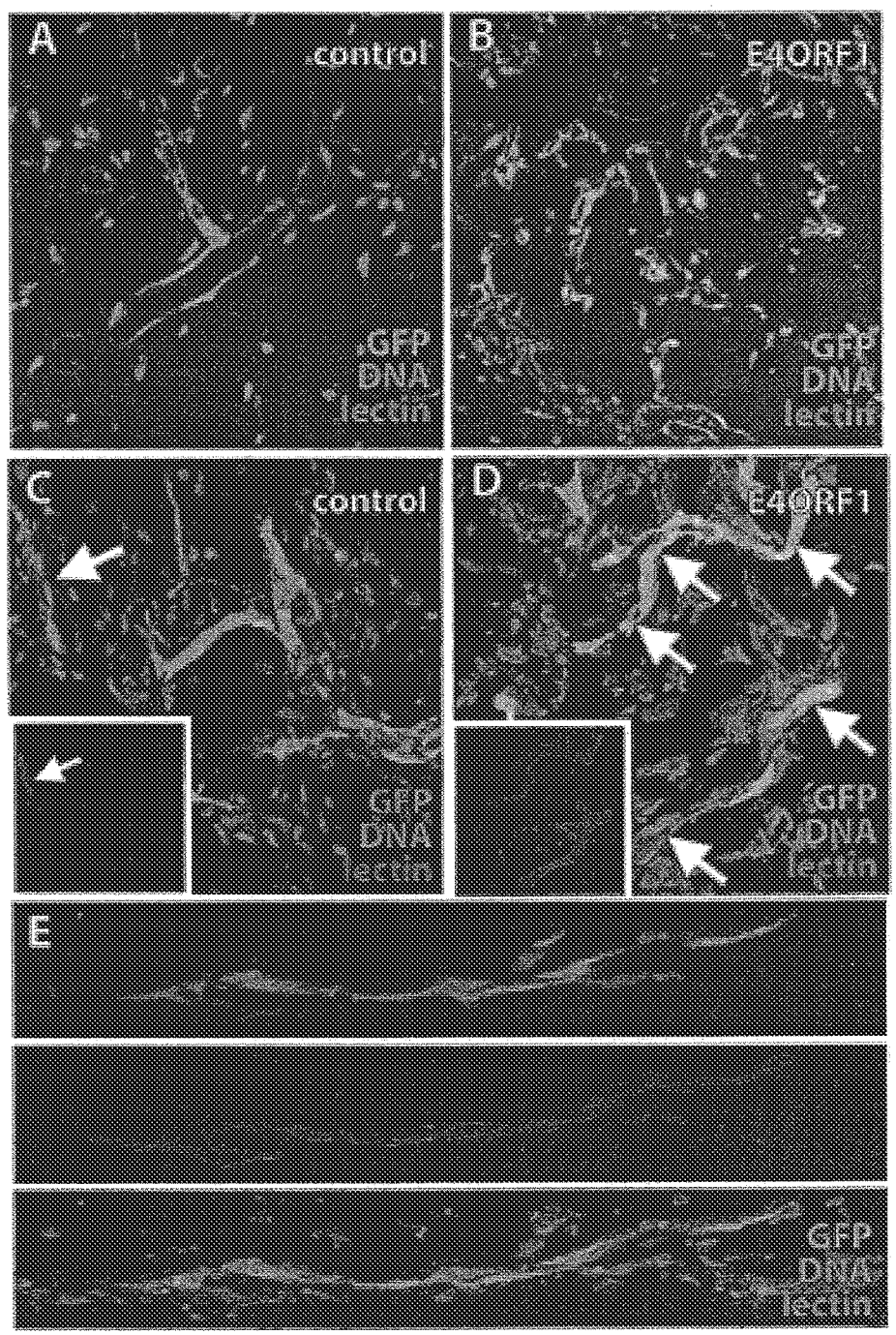
FIGS. 5A-I show that E4ORF1-expressing endothelial cells (ECs) are capable of tubulogenesis, sprouting and supporting leukemic cell growth. Mice received subcutaneous inoculation of 10×10$^6$ GFP-expressing ECs (control) (FIGS. 5A and 5C) or ECs expressing both GFP and E4ORF1 (FIGS. 5B, 5D and 5E). The mice were administered intravenously human specific-UEA-1 lectin just prior to sacrifice 14 days after subcutaneous inoculation of the ECs. Cryosections were stained to detect UEA-1 as a measure of vessels that were functional at the time of sacrifice.

In order to determine the capacity of E4ORF1-expressing ECs to assemble into functional vessels in the Matrigel™ implants in vivo, monolayers of E4ORF1 ECs (transduced by Lenti-E4ORF1) or naïve ECs were labeled with Lenti-GFP. Ten million of either cell type were inoculated with Matrigel™ into the flanks of NOD-SCID mice. Vessels were given two weeks to assemble in the plugs at which point, the mice were injected intravenously with human endothelium-specific UEA-1 lectin to examine functionality of the vessels and the presence of human derived GFP-positive functional neo-vessels within the Matrigel™. The results were evaluated by stereo confocal microscopy. Similar to naïve ECs (FIGS. 5A and C), ECs expressing E4ORF1 (FIGS. 5B and D) were able to assemble into functional, branching GFP$^+$, lectin$^+$ neo-vessels connecting to the host vessel (FIGS. 5C and D). ECs expressing E4ORF1 also gave rise to long sprouting GFP$^+$ lectin$^+$ neo-vessels (FIG. 5E). These data suggest that E4ORF1-expressing ECs maintain their angiogenic repertoire and can assemble into neo-vessels, even in the absence of exogenous growth factors.

E4ORF1-Expressing ECs Can Assemble into Neo-Vessels in Leukemic Xenografts

Figures 5F, 5G, 5H, 5I:
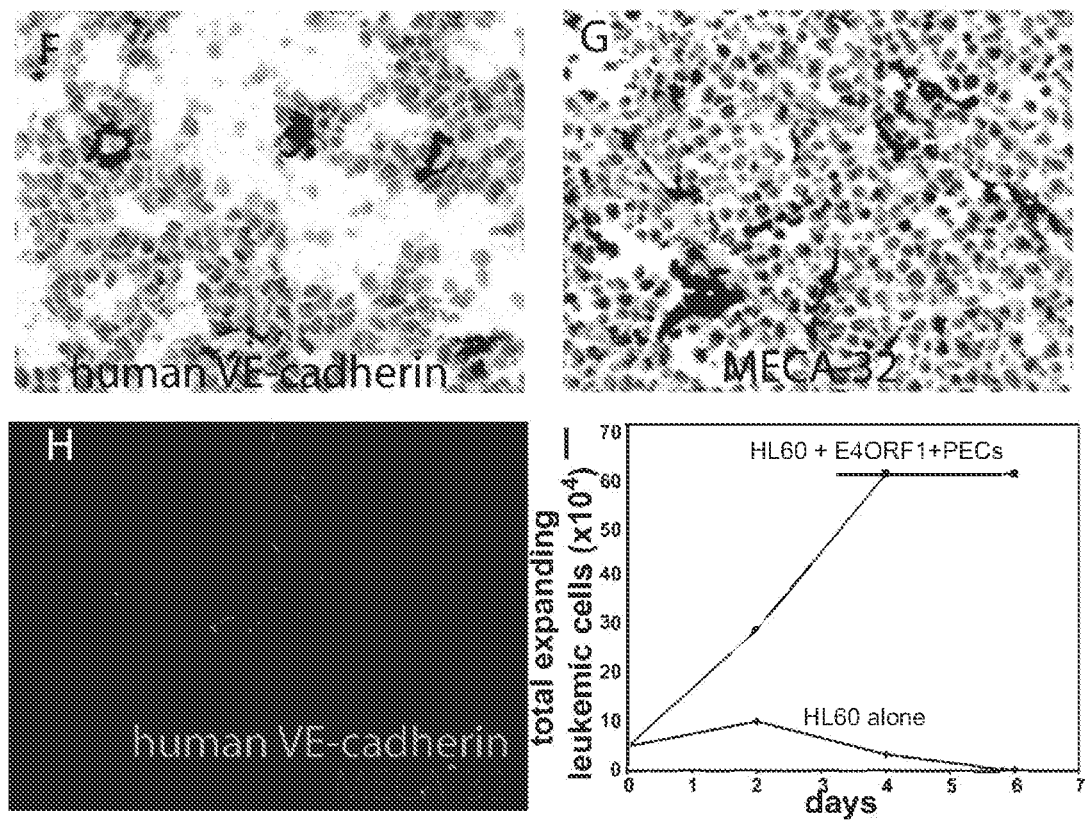

As an alternative means to assess the pro-angiogenic properties of E4ORF1-expressing EC in vivo, human HL60 leukemia cells were combined with E4ORF1-expressing ECs in NOD-SCID mice subcutaneously. Whereas normal ECs do not survive within human tumor xenografts, the human VE-cadherin$^+$ E4ORF1 ECs not only survived for at least 10 days within the HL60 tumors, but also formed vessel-like structures with a lumen (FIGS. 5F and G). Double labeling for mouse (MECA-32) and human (VE-cadherin) endothelium confirmed not only the species specificity of the antibodies but also revealed formation of E4ORF1-expressing vessels within the tumor. These data reveal the propensity of E4ORF1 to induce a pro-angiogenic phenotype in endothelial cells in vivo in either a benign setting or in tumors.

E4ORF1 Expression in ECs Supports the Expansion of Leukemic Cells in Serum-Free, Growth Factor-Free Conditions To determine whether ECs in serum-free, growth factor-free conditions can induce proliferation in leukemic HL60 cells, HL60 cells were grown in serum-free, cytokine-free conditions as well as in co-culture with E4ORF1-expressing ECs. In serum-free, cytokine-free conditions, HL60 cells underwent apoptosis (FIG. 5I). However, culture of the HL60 cells with E4ORF1 ECs in serum-free, cytokine-free conditions resulted in a remarkable expansion of HL60 cells (FIG. 5I). During the culture period, E4ORF1 ECs maintained their integrity, facilitating proliferation of the leukemic cells. This demonstrates the ability of ECs to support the expansion of leukemic cells without addition of exogenous cytokines.

Discussion

E4 gene of the adenoviral vector plays an important role in promoting survival of ECs and regulating angiogenic potential of ECs by recruiting the VE-cadherin/Akt-signaling cascade. Remarkably, this pro-survival effect of the E4 gene is restricted to vascular cells but not mesenchymal cells. The specific E4ORF gene that enhances the pro-angiogenic effect of the ECs has been identified. Among the six potential gene products transcribed by the E4ORFs of adenoviral E4 gene, the E4ORF1 gene potentiates the survival and migration of ECs, both in vitro and in vivo. The pro-angiogenic effect of E4ORF1 conferred to ECs is mediated through the activation of PI3K-mTOR and Akt signaling pathway. Remarkably, inhibition of mTOR is highly effective in blocking pro-angiogenic effect afforded by the E4ORF1 gene. Moreover, FGF-2 expression is increased by infection with E4ORF1-infected ECs leading to stimulation of angiogenesis both in vivo and in vitro. These results show that the E4ORF1 protein augments the survival of ECs through recruiting FGF-2 and activation of pro-angiogenic signaling pathways.

In addition to maintaining the angiogenic effect of ECs, E4ORF1-expressing ECs can also contribute to angiogenesis in leukemic chloromas. ECs infected with E4ORF1 supported long term expansion of leukemic cells under serum-free, growth factor-free conditions, without themselves undergoing apoptosis. Thus, the survival and angiogenic effects of ECs expressing E4ORF1 were sustained without immortalization of such cells. This has allowed the culture of pure populations of organ-specific ECs from testis and umbilical cord blood. Thus, E4ORF1 facilitates the isolation of intact organ-specific endothelial cells to examine their potential in regulating vascularization of regenerating organs, and identify the mechanism by which ECs contribute to tumor neovascularization.

Adenovirus gene transfer vectors carrying the full compliment of the E4 gene activates PI3K in ECs and other cell types (Zhang et al. (2004) *J Biol Chem* 279(12):11760-66; Rajala et al. (2005) *J Virol* 79(19):12332-41; Liu et al. (2005) *J Virol* 79(23):14507-15). The invention provides that E4ORF1 protein is an essential product for adenovirus E4-mediated activation of PI3K. Activating PI3K by E4ORF1 resulted in increased RhebGTP loading and stimulating mTOR activity (O'Shea et al. (2005) *Embo J* 24(6): 1211-21). PI3K/mTOR signaling pathway seem to play a critical role in mediating survival, replication, and migration of mammalian cells (Brunet et al. (2001) *Curr Opin Neurobiol* 11(3):297-305). Inhibition of mTOR by rapamycin only partially reversed the E4ORF1 effect of promoting EC survival, indicating that mTOR may not be a unique signal pathway for the E4ORF1 effect (FIG. 2B). Indeed, the invention provides that E4ORF1 increased FGF-2 synthesis in EC. Activation of Src and PI3K-Akt signaling may target in parallel with FGF-2 expression in an mTOR-independent manner (Zhang et al. (2006) *J Biol Chem* 281(2):905-14). Thus, the results indicate that E4ORF1 drives EC survival and angiogenesis via mTOR-dependent and an additional mTOR-independent signal pathway.

Exposure of survival factors, such as FGF-2 and VEGF-A, is important for maintaining EC survival and migration (Meredith et al. (1993) *Mol Biol Cell* 4(9): 953-61). These growth factors have been shown to be important in initiating neo-angiogenesis (Veikkola et al. (2000) *Cancer Res* 60(2): 203-12; Seghezzi et al. (1998) *J Cell Biol* 141(7): 1659-73). E4ORF1 product has been shown in this invention to increase FGF-2 expression in EC monolayers. However, significant changes of VEGF-A expression in ECs were not detectable by ELISA and Western blot. Thus, the effect of E4ORF1 on the angiogenic process can result from an increase in endogenous FGF-2 expression. FGF-2 serves both paracrine and autocrine functions in the regulation of angiogenesis. Overexpression of endogenous FGF-2 in vivo has significant pro-angiogenic effect, increasing capillary density and improving cardiac resistance to injury (Sheikh et al. (2001) *Am J Physiol Heart Circ Physiol* 280(3):H1039-1050), whereas FGF-2 knockout mice exhibit significant delay in the rate of healing of full-thickness excisional skin wounds (Ortega et al. (1998) *Proc Natl Acad Sci USA* 95(10):5672-7). Studies have shown that FGF-2 is a downstream target of PI3K in many important cellular pathways (Zhang et al. (2006) *J Biol Chem* 281(2):905-14; Weylie et al. (2006) *J Vasc Res* 43(1):61-9). However, FGF-2 can also activate PI3K/Akt signaling pathway (Vandermoere et al. (2005) *Oncogene* 24(35):5482-91). Thus, FGF2-activated Akt pathway may involve a positive feedback loop. Indeed, E4ORF1 activated both PI3K and FGF-2 expression, and thus, exerting a synergistic effect on EC survival and angiogenesis.

Adenovirus E4ORF1 has been identified interacting with several different cellular PDZ proteins, including MAGI-1, MUPP1 and ZO-2 (Glaunsinger et al. (2000) *Oncogene* 19(46):5270-80; Songyang et al. (1997) *Science* 275(5296): 73-7). PDZ proteins regulate cell growth, polarity, and adhesion in response to cell contact (Craven and Bredt (1998) *Cell* 93(4):495-8; Fanning and Anderson (1999) *J Clin Invest* 103(6):767-72). MAGI-1 formation of complexes with B-catenin and E-cadherin might contribute to the formation of adherens molecular complexes at tight junctions in endothelial and epithelial cells (Wegmann et al. (2004) *Exp Cell Res* 300(1):121-33; Dobrosotskaya and James (2000) *Biochem Biophys Res Commun* 270(3):903-9). Overexpression of the N-terminal domain of ZO-1 in connexin 43-expressing cells resulted in redistribution of connexin 43 from cell-cell interfaces to cytoplasmic structures (Toyofuku, et al. (1998) *J Biol Chem* 273(21):12725-31). Consistent with these results, it was demonstrated that AdE4 activated the VE-cadherin/Akt pathway and modulated connexin 40 and 43 expression (Zhang et al. (2004) *J Biol Chem* 279(12):11760-66; Zhang et al. (2005) *Circ Res* 96(9):950-7).

E4ORF1 activates PI3K and FGF-2 pathways to enhance the survival and induce neo-angiogenesis in ECs. These findings show that the E4ORF1 product possesses a potential novel role for AdE4 in regulation of angiogenesis and survival of ECs in vitro and in vivo. In one aspect of the invention, E4ORF1 can be used as an intracellular decoy to delineate pro-angiogenic pathways mediating assembly of new vessels. As such, infection of E4ORF1 can be exploited to induce revascularization of the ischemic tissues.

Virulent adenoviruses are evolved to hijack the molecular machinery of the host cells, such as endothelial cells, to replicate the viral genome, while keeping the host cell alive. The discovery of this invention has taken advantage of the capacity of adenoviral E4 gene complex to activate cell survival signals, in order to identify gene products that can preserve long-term endothelial cell integrity. Among the six gene products transcribed by the adenoviral E4 gene complex, the invention provides the discovery that the E4ORF1 gene product is the key gene that endows endothelial cells with the capacity to survive and proliferate in a contact-inhibited manner and preserves their neo-angiogenic potential, all in the absence of serum or endothelial cell growth factor supplements. E4ORF1-expressing ECs maintained the complete angiogenic profile of ECs and assembled into functional neo-vessels in vitro and in vivo and contributed to angiogenesis in leukemic chloromas. Although naïve ECs underwent apoptosis within 6 hours in cytokine- and serum-free conditions, E4ORF1-expressing ECs supported long-term expansion of leukemic cells under serum- and cytokine-free conditions, without themselves undergoing apoptosis. Through tonic stimulation of PI3K-Akt-mTOR activating the FGF-2/FGFR-1 pathway, E4ORF1-expressing ECs supported the sustenance of the angiogenic phenotype without immortalization. This approach has also permitted the culture of pure populations of organ-specific ECs from testis and umbilical cord blood. As such E4ORF1 facilitates isolation of intact organ-specific endothelial cells to examine their potential in regulating vascularization of regenerating organs, and to define the mechanisms by which endothelial cells contribute to tumor neo-angiogenesis. Importantly, this enables for the first time the use of minimal media conditions (i.e., exogenous cytokine- and serum-free media) in the assay of endothelial-derived signals that support cancer or normal stem cell self-renewal.

Evidence indicates that organ-specific endothelial cells are not only conduits for delivery of oxygen and nutrients, but also they provide a permissive environment for the survival and growth of organ-specific stem and progenitor cells (Rafii et al. (1995) *Blood* 86:3353-63; Lammert et al. (2001) *Science* 294:564-7; Rafii, S., et al. (1994) *Blood* 84:10-19; Kiel et al. (2005) *Cell* 121:1109-21; Avecilla et al. (2004) *Nat Med* 10:64-71; Yoshida et al. (2007) *Science* 317:1722-26; Nikolova et al. (2006) *Dev Cell* 10:397-405; Dias et al. (2001) *Proc Natl Acad Sci USA* 98:10857-62; Gilbertson & Rich (2007) *Nat Rev Cancer* 7:733-6; Calabrese et al. (2007) *Cancer Cell* 11:69-82). Based on primarily in vivo studies, ECs have been shown to elaborate membrane or soluble cytokines (Rafii et al. (1995) *Blood* 86:3353-63; Avecilla et al. (2004) *Nat Med* 10:64-71; Yoshida et al. (2007) *Science* 317:1722-26; Dias et al. (2001) *Proc Natl Acad Sci USA* 98:10857-62; Calabrese et al. (2007) *Cancer Cell* 11:69-82) or deposit unique matrix (Nikolova et al. (2006) *Dev Cell* 10:397-405) that contribute to the specification and differentiation of organ-specific stem cells. The use of immortalized endothelial cells lines has manifested marginal benefit in elucidating the factors that support tumorigenesis. In addition, culture of ECs, in the absence of an enriched cocktail of pro-angiogenic factors results in the apoptosis of ECs within a few hours, precluding further study. Indeed, the contribution of ECs to stem and progenitor cell biology has been obscured by the presence of stem cell-active cytokines, including FGFs, VEGFs, TGF-β and EGFs, which can by themselves promote the survival of stem and tumor cells. In fact, it is not clear in previous published studies (Rafii et al. (1995) *Blood* 86:3353-63; Nikolova et al. (2006) *Dev Cell* 10:397-405; Shen et al. (2004) *Science* 304:1338-40) whether proliferation of stem cells was mediated by elaboration of factors by endothelial cells or by exogenously added FGFs, and EGFs. Therefore, the unique capacity of the compositions and methods of the invention to maintain the neo-angiogenic state of ECs without the otherwise ubiquitous requirement for numerous exogenous cytokines provides for a radically different in vitro platform to identify and characterize the factors that promote the growth of stem and tumor cells. In addition, introduction of the E4ORF1 compositions of the invention allows for purification of organ specific endothelial cells. To date, isolation of endothelial cells from human and mouse tissues, including testis and lung has been achieved. These findings provide a technical advance in the study of the heterogeneity of endothelial cells without compromising their neo-angiogenic integrity.

The ability to induce neo-angiogenesis by E4ORF1 and the compositions of the invention without oncogenic transformation is a unique feature of the E4ORF1 gene product that is primarily conferred to the human endothelial cells. E4ORF1 cloned from either type 5 or 9 adenoviruses had no oncogenic effect, and E4ORF1-expressing ECs maintained both contact inhibition and the requirement for exogenous FGF-2 to proliferate. The pro-angiogenic effect of E4ORF1 conferred to ECs was mediated through the activation of PI3K-mTOR and Akt signaling pathway. Inhibition of mTOR was highly effective in blocking the pro-angiogenic effect afforded by the E4ORF1 gene. Moreover, FGF-2 expression was increased by expression of E4ORF1 in ECs, leading to stimulation of angiogenesis both in vivo and in vitro. These results suggest that the E4ORF1 protein augments the survival of ECs by activation of FGF-2/FGFR-1 pro-angiogenic signaling pathways without oncogenic transformation.

This invention provides the finding that E4ORF1 can induce tonic activation of Akt. This is important, since naive ECs require chronic stimulation with a wide variety of growth factors, including VEGF-A, FGF-2 and EGF, in order to maintain activation of Akt and cell proliferation. In fact, VEGF-A or FGF-2 stimulation of naïve ECs results in phosphorylation of Akt for only 10 minutes, with rapid dephosphorylation and activation of the apoptotic pathway, if the cells are not stimulated again with growth factors. However, E4ORF1-expressing ECs maintained Akt phosphorylation indefinitely, showing that E4ORF1 gene product can interfere with regulatory pathways to deactivate Akt or, alternatively, can induce constant activation of Akt through a novel recruitment of the PI3K-mTOR pathway. As rapamycin was only partially effective in reversing the pro-survival effect of E4ORF1, these data show that other pathways drive E4ORF1-activation of Akt. Akt-mediated upregulation of FGF-2 can contribute to persistent activation of PI3K through an intrakine FGF-2/FGFR-1 activation.

The mechanism by which E4ORF1 activates Akt is complex and involves an interaction with cytoskeletal regulatory elements. E4ORF1 isolated from adenovirus type 9, which has primarily been studied in mouse stromal cells, has been found to interact with several different cellular PDZ proteins, including Dlg1, MAGI-1, MUPP1 and ZO-2 (Glaunsinger et al. (2000) Oncogene 19:5270-80; Frese et al. (2003) Oncogene 22:710-21). PDZ proteins regulate cell growth, polarity, and adhesion in response to cell contact. In mouse stromal cells, specific binding of E4ORF1 to endogenous Dlg1 promotes Ras-mediated PI3K activation (Frese et al. (2003) Oncogene 22:710-21). Formation of complexes containing MAGI-1, β-catenin, and E-cadherin can contribute to the formation of adherens molecular complexes at tight junctions in endothelial and epithelial cells. All together, activation of this cascade of events could result in chronic activation of Akt without cellular transformation. Consistent with these results, it was demonstrated that AdE4 activated the VE-cadherin/Akt pathway and modulated connexin 40 and 43 expression (Zhang et al. (2004) J Biol Chem 279:11760-6; Zhang et al. (2005) Circ Res 96:950-7). Therefore, interaction of E4ORF1 protein and PDZ can play an initial role in regulation of survival and angiogenesis in human ECs, as well.

An advantage of the invention is reproducible maintenance of the angiogenic state of the E4ORF1-expressing ECs. This permanent and robust angiogenic state, which has never been reported by other gene transduction approaches is most likely due to persistent activation of Akt. Remarkably, the physiological effect of E4ORF1 was pronounced in endothelial but not smooth muscle, hematopoietic cells or even tumor cells. Indeed, numerous studies have shown that activation of Akt plays a critical role in modulation of the angiogenic state in endothelial cells (Chen et al. (2005) Nat Med 11:1188-11; Ackah et al. (2005) J Clin Invest 115:2119-27; Phung et al. (2006) Cancer Cell 10:159-70; Mukai et al. (2006) J Clin Invest 116:334-43; Phung et al. (2007) Cancer Res 67:5070-5; Somanath et al. (2007) J Biol Chem 282: 22964-76). The extent of Akt activation dictates the level of angiogenic activity. Over-expression of Akt results in induction of neo-angiogenesis, vascular leakiness, and enhanced tumor growth (Phung et al. (2006) Cancer Cell 10:159-70). In contrast, absence of Akt1 may affect the stability and patterning of neo-angiogenesis (Ackah et al. (2005) J Clin Invest 115:2119-27). Therefore, the chronic low level activation of Akt afforded by E4ORF1 provides the precise signals to confer to E4ORF1-expressing ECs a long-lasting angiogenic state, without dysregulated growth.

Exposure to survival factors, such as FGF-2 and VEGF-A, is important for maintaining EC survival and migration (Rafii et al. (1995) Blood 86:3353-63). These growth factors have been shown to be important in initiating neo-angiogenesis. Here, the E4ORF1 product increased FGF-2 expression, survival and proliferation of EC monolayers. VEGF-A has only a marginal effect on increasing proliferation of E4ORF1-expressing ECs. The effect of E4ORF1 on the angiogenic process can result from an increase in endogenous FGF-2 expression. FGF-2 serves both paracrine (Chung et al. (2007) J Virol 81:4787-97) and autocrine functions in the regulation of angiogenesis. Overexpression of endogenous FGF-2 in vivo has a significant pro-angiogenic effect, increasing capillary density and improving cardiac resistance to injury. FGF-2 is a downstream target of PI3K in many important cellular pathways (Zhang et al. (2006) J Biol Chem 281:905-14; Weylie et al. (2006) J Vasc Res 43:61-69). FGF-2 can also activate the PI3K/Akt signaling pathway. The FGF-2-activated Akt pathway can involve a positive feedback loop. E4ORF1 activated both PI3K and FGF-2 expression, thus exerting a synergistic effect on EC survival and angiogenesis.

The E4ORF1 adenoviral gene, through chronic activation of the FGF-2/PI3K-Akt-mTOR pathway, enhanced survival, and maintained neo-angiogenesis in ECs without cellular transformation. The E4ORF1 gene product supported survival of the ECs in the absence of growth factors and serum but exogenous stimulation with FGF-2 was still needed to induce contact inhibited proliferation. The compositions of the invention can hijack pro-angiogenic signals of the host endothelium and enhance their invasiveness and establish their pathological damage to the infected tissues. In addition, E4ORF1 organ specific EC cultures provide methods to decipher the unique molecular and cellular pathways activated in neo-angiogenic endothelium that support organogenesis and tumorigenesis.

Example 2

E4ORF1-Expressing Feeder Cells

Figure 6:
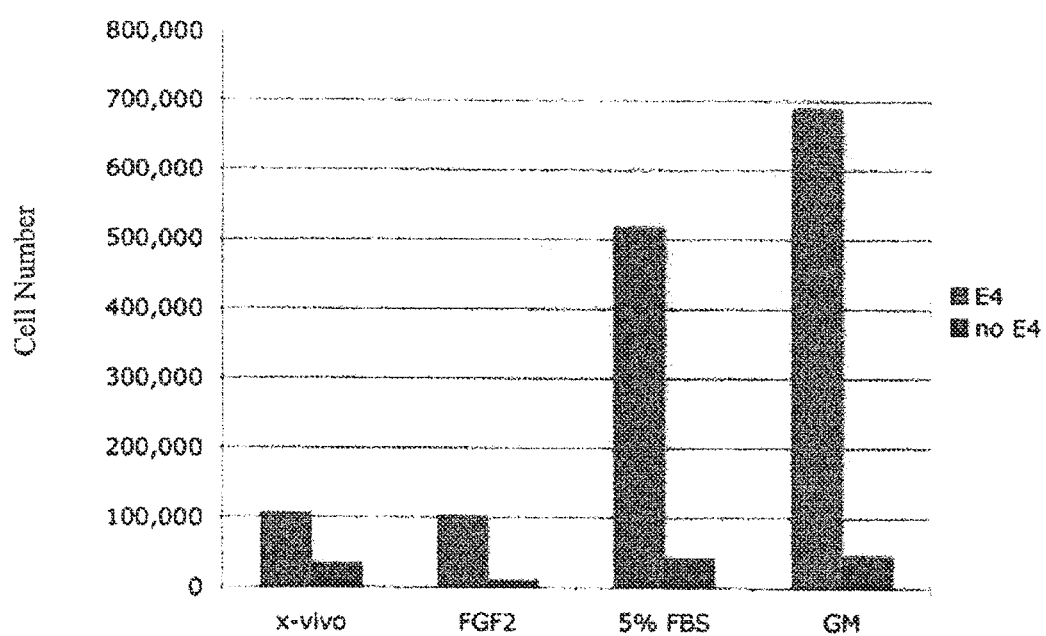
FIG. 6 provides a graph showing that a feeder cell layer of E4ORF1-transduced endothelial cells induced expansion of CD34+ hematopoetic progenitor cells grown on this feeder cell over a five week period even in the absence of serum. The number of cells is indicated on X axis. The various cytokine treatments are indicated on the Y axis. "x-vivo" represents the basal medium, "FGF2" refers to medium supplemented with basic fibroblast growth factor, "5% FBS" refers to medium supplemented with 5% fetal bovine serum, and "GM" refers to medium supplemented with granulocyte monocyte colony stimulating factor.

Stem and progenitor cells are notoriously difficult to maintain and grow in culture. Many such cells must be grown with "feeder cells". For example, feeder layers comprising primary endothelial cells can be used to support the growth of hematopoietic stem cells. However, these feeder layers of primary endothelial cells generally require the presence of serum or growth factors for long-term maintenance. Many stem cells cannot tolerate the presence of serum or certain growth factors. Experiments were performed to determine whether E4ORF1-expressing endothelial cells would be useful as feeder cells to support the growth of stem cells and progenitor cells such as hematopoietic stem or progenitor cells. FIG. 6 provides a graph showing that a feeder cell layer of E4ORF1-transduced endothelial cells induced expansion of CD34+ hematopoietic progenitor cells over a five-week period, even in the absence of serum.

We claim:

1. An isolated population of human umbilical vein endothelial cells (HUVECs) that:

a. comprise a recombinant nucleic acid molecule that encodes an adenovirus type 5 E4ORF1 protein, and b. do not comprise a nucleic acid sequence that comprises an entire adenovirus E4 region.

2. The isolated population of claim 1, wherein the HUVECS do not comprise adenovirus E4ORF2, E4ORF3, E4ORF4, E4ORF5, E4ORF6, or E4ORF6/7, nucleic acid sequences.

3. The isolated population of claim 1, wherein the recombinant nucleic acid molecule that encodes the adenovirus type 5 E4ORF1 protein comprises a sequence having at least 97% sequence identity to SEQ ID NO. 1.

4. The isolated population of claim 1, wherein the recombinant nucleic acid molecule that encodes the adenovirus type 5 E4ORF1 protein comprises a sequence having at least 98% sequence identity to SEQ ID NO. 1.

5. The isolated population of claim 1, wherein the recombinant nucleic acid molecule that encodes the adenovirus type 5 E4ORF1 protein comprises SEQ ID NO. 1.

6. The isolated population of claim 1, wherein the recombinant nucleic acid molecule is comprised within a viral vector.

7. The isolated population of claim 6, wherein the viral vector is selected from the group consisting of an adenoviral vector, an adeno-associated virus vector, a retroviral vector, and a herpesvirus vector.

8. The isolated population of claim 7, wherein the viral vector is a retroviral vector.

9. The isolated population of claim 8, wherein the retroviral vector is a lentiviral vector.

10. A composition comprising:
    a. a population of human umbilical vein endothelial cells (HUVECs) that:
       i. comprise a recombinant nucleic acid molecule that encodes an adenovirus type 5 E4ORF1 protein, and
       ii. do not comprise a nucleic acid sequence that comprises an entire adenovirus E4 region, and
    b. a carrier solution.

11. The composition of claim 10, wherein the carrier solution comprises a physiological saline or one or more other therapeutically acceptable agents.

12. The composition of claim 10, wherein the HUVECS do not comprise adenovirus E4ORF2, E4ORF3, E4ORF4, E4ORF5, E4ORF6, or E4ORF6/7, nucleic acid sequences.

13. The composition of claim 12, wherein the carrier solution comprises a physiological saline or one or more other therapeutically acceptable agents.

14. The composition of claim 10, wherein the recombinant nucleic acid molecule that encodes the adenovirus type 5 E4ORF1 protein comprises a sequence having at least 97% sequence identity to SEQ ID NO. 1.

15. The composition of claim 10, wherein the recombinant nucleic acid molecule that encodes the adenovirus type 5 E4ORF1 protein comprises a sequence having at least 98% sequence identity to SEQ ID NO. 1.

16. The composition of claim 10, wherein the recombinant nucleic acid molecule that encodes the adenovirus type 5 E4ORF1 protein comprises SEQ ID NO. 1.

17. The composition of claim 10, wherein the recombinant nucleic acid molecule is comprised within a viral vector.

18. The composition of claim 17, wherein the viral vector is selected from the group consisting of an adenoviral vector, an adeno-associated virus vector, a retroviral vector, and a herpesvirus vector.

19. The composition of claim 18, wherein the viral vector is a retroviral vector.

20. The composition of claim 19, wherein the retroviral vector is a lentiviral vector.

\* \* \* \* \*